United States Patent
Mitha et al.

(10) Patent No.: US 12,419,764 B2
(45) Date of Patent: Sep. 23, 2025

(54) BIOABSORBABLE FLOW DIVERTING SCAFFOLD

(71) Applicant: Fluid Biomed Inc., Calgary (CA)

(72) Inventors: Alim P. Mitha, Calgary (CA); John H. Wong, Calgary (CA); Mehdi Jamshidi, Calgary (CA)

(73) Assignee: Fluid Biomed Inc., Calgary (CA)

( * ) Notice: Subject to any disclaimer, the term of this patent is extended or adjusted under 35 U.S.C. 154(b) by 282 days.

(21) Appl. No.: 16/810,679

(22) Filed: Mar. 5, 2020

(65) Prior Publication Data
US 2020/0229954 A1 Jul. 23, 2020

Related U.S. Application Data

(63) Continuation of application No. PCT/CA2019/050304, filed on Mar. 12, 2019.

(60) Provisional application No. 62/641,891, filed on Mar. 12, 2018.

(51) Int. Cl.
*A61F 2/90* (2013.01)

(52) U.S. Cl.
CPC ........ *A61F 2/90* (2013.01); *A61F 2210/0004* (2013.01); *A61F 2210/0014* (2013.01); *A61F 2210/0057* (2013.01); *A61F 2250/0098* (2013.01)

(58) Field of Classification Search
CPC ....................................................... A61F 2/07
See application file for complete search history.

(56) References Cited

U.S. PATENT DOCUMENTS

| | | | |
|---|---|---|---|
| 4,475,972 A | 10/1984 | Wong | |
| 5,551,954 A | 9/1996 | Buscemi et al. | |
| 6,463,317 B1 | 10/2002 | Kucharczyk et al. | |
| 6,626,939 B1 * | 9/2003 | Burnside | A61L 31/148 623/1.38 |
| 6,652,570 B2 | 11/2003 | Smith et al. | |
| 6,712,834 B2 | 3/2004 | Yassour et al. | |
| 6,740,105 B2 | 5/2004 | Yodfat et al. | |
| 6,827,735 B2 | 12/2004 | Greenberg | |
| 6,866,680 B2 | 3/2005 | Yassour et al. | |
| 7,011,678 B2 | 3/2006 | Tenerz et al. | |
| 7,069,835 B2 | 7/2006 | Nishri et al. | |
| 7,093,527 B2 | 8/2006 | Rapaport et al. | |
| 7,232,459 B2 | 6/2007 | Greenberg et al. | |

(Continued)

FOREIGN PATENT DOCUMENTS

| | | |
|---|---|---|
| AU | 2013216587 B2 | 8/2013 |
| EP | 1786358 B1 | 4/2013 |

(Continued)

OTHER PUBLICATIONS

Adeeb, et al., "Risk of Branch Occlusion and Ischemic Complications with the Pipeline Embolization Device in the Treatment of Posterior Circulation Aneurysms," American Journal of Neuroradiology, vol. 39, No. 7, 2018, pp. 1303-1309.

(Continued)

*Primary Examiner* — Jacqueline Woznicki

(57) ABSTRACT

This disclosure relates to scaffolds made of a braid of bioabsorbable polymeric fibers for implantation within a lumen of a mammalian body and, in particular, to such scaffolds that are configured to divert blood flow from a pathology associated with a blood vessel.

18 Claims, 21 Drawing Sheets

(56) References Cited

U.S. PATENT DOCUMENTS

| | | | |
|---|---|---|---|
| 7,275,471 | B2 | 10/2007 | Nishri et al. |
| 7,306,624 | B2 | 12/2007 | Yodfat et al. |
| 7,637,939 | B2 | 12/2009 | Tischler |
| 7,686,842 | B2 | 3/2010 | Pavcnik et al. |
| 8,211,168 | B2 | 7/2012 | Purdy et al. |
| 8,267,986 | B2 | 9/2012 | Berez et al. |
| 8,303,650 | B2 | 11/2012 | Shokoohi |
| 8,317,857 | B2 | 11/2012 | Shokoohi et al. |
| 8,394,136 | B2 | 3/2013 | Hartley et al. |
| 8,419,787 | B2 | 4/2013 | Yodfat et al. |
| 8,506,619 | B2 | 8/2013 | Ortiz et al. |
| 8,623,073 | B2 | 1/2014 | Klocke et al. |
| 8,628,564 | B2 | 1/2014 | Berez et al. |
| 8,715,312 | B2 | 5/2014 | Burke et al. |
| 8,876,886 | B2 | 11/2014 | Kaufmann et al. |
| 9,005,269 | B2 | 4/2015 | Armstrong et al. |
| 9,155,641 | B2 | 10/2015 | Schaeffer et al. |
| 9,198,668 | B2 | 12/2015 | Theobald et al. |
| 9,216,100 | B2 * | 12/2015 | Seibold ............... D03D 13/004 |
| 9,445,926 | B2 | 9/2016 | Jang |
| 9,526,642 | B2 | 12/2016 | Arnault De La Menardiere et al. |
| 9,615,832 | B2 | 4/2017 | Bose et al. |
| 9,808,359 | B2 | 11/2017 | Ferrera et al. |
| 9,833,343 | B2 | 12/2017 | Burnside et al. |
| 9,855,371 | B2 | 1/2018 | Scanlon et al. |
| 9,931,193 | B2 | 4/2018 | Cully et al. |
| 10,098,766 | B2 | 10/2018 | Harder |
| 11,389,311 | B2 | 7/2022 | Slazas et al. |
| 2002/0165597 | A1 | 11/2002 | Clerc et al. |
| 2003/0100940 | A1 | 5/2003 | Yodfat |
| 2003/0100945 | A1 | 5/2003 | Yodfat et al. |
| 2004/0010307 | A1 | 1/2004 | Grad et al. |
| 2004/0049204 | A1 | 3/2004 | Harari et al. |
| 2004/0122468 | A1 | 6/2004 | Yodfat et al. |
| 2004/0133129 | A1 | 7/2004 | Harari et al. |
| 2004/0167598 | A1 * | 8/2004 | Margolis ................... A61F 2/91 623/1.11 |
| 2004/0199243 | A1 | 10/2004 | Yodfat |
| 2004/0267281 | A1 | 12/2004 | Harari et al. |
| 2005/0267562 | A1 | 12/2005 | Jones et al. |
| 2007/0016233 | A1 | 1/2007 | Ferrera et al. |
| 2007/0021816 | A1 | 1/2007 | Rudin |
| 2007/0203564 | A1 | 8/2007 | Rusk et al. |
| 2008/0221670 | A1 * | 9/2008 | Clerc ....................... A61F 2/07 623/1.34 |
| 2008/0281350 | A1 | 11/2008 | Sepetka et al. |
| 2008/0281393 | A1 | 11/2008 | Armstrong et al. |
| 2009/0182404 | A1 | 7/2009 | Shokoohi |
| 2009/0306704 | A1 * | 12/2009 | Johnson ................... A61F 2/01 606/200 |
| 2010/0010621 | A1 | 1/2010 | Klocke |
| 2011/0282428 | A1 | 11/2011 | Meyer et al. |
| 2012/0143300 | A1 | 6/2012 | Palasis et al. |
| 2012/0316638 | A1 | 12/2012 | Grad et al. |
| 2013/0053872 | A1 | 2/2013 | Hansen |
| 2013/0060327 | A1 | 3/2013 | Shokoohi et al. |
| 2013/0226277 | A1 | 8/2013 | Sun et al. |
| 2015/0209133 | A1 | 7/2015 | Cam et al. |
| 2016/0045304 | A1 * | 2/2016 | Orion ..................... A61B 17/11 623/1.13 |
| 2016/0143756 | A1 | 5/2016 | Rezac et al. |
| 2016/0206419 | A1 * | 7/2016 | Hebert ................... B29D 23/00 |
| 2016/0206452 | A1 * | 7/2016 | Berez ............... A61B 17/12118 |
| 2017/0224476 | A1 | 8/2017 | You et al. |
| 2018/0200041 | A1 | 7/2018 | Rasmussen et al. |
| 2018/0206852 | A1 | 7/2018 | Moeller |
| 2019/0110881 | A1 * | 4/2019 | Heiferman ............... A61F 2/01 |
| 2022/0257838 | A1 * | 8/2022 | Mitha ..................... A61F 2/07 |
| 2023/0321325 | A1 * | 10/2023 | Mitha ................... A61L 31/06 623/1.15 |

FOREIGN PATENT DOCUMENTS

| | | |
|---|---|---|
| EP | 3765106 B1 | 2/2024 |
| JP | H11197252 A | 7/1999 |
| JP | 2012055649 A | 3/2012 |
| JP | 2014176656 A | 9/2014 |
| JP | 2017535379 A | 11/2017 |
| WO | WO-2006022948 A1 | 3/2006 |
| WO | WO-2016086195 A1 | 6/2016 |
| WO | WO-2017165889 A2 | 9/2017 |
| WO | WO-2019173912 A1 | 9/2019 |

OTHER PUBLICATIONS

Alderazi, et al., "Flow Diverters for Intracranial Aneurysms," Stroke Research and Treatment, vol. 2014, 2014, 13 pages.

Anton-Pacheco, et al., "Initial experience with a new biodegradable airway stent in children: Is this the stent we were waiting for?," Pediatric Pulmonology, vol. 51, No. 6, 2016, pp. 607-612.

Augsburger, et al., "Effect of Flow Diverter Porosity on Intraaneurysmal Blood Flow," Clinical Neuroradiology, vol. 19, 2009, pp. 204-214.

Bederson, et al., "Guidelines for the management of aneurysmal subarachnoid hemorrhage: a statement for healthcare professionals from a special writing group of the Stroke Council, American Heart Association," Stroke, vol. 40, No. 3, 2009, pp. 994-1025.

Bedoya, et al., "Effects of stent design parameters on normal artery wall mechanics," Journal of Biomechanical Engineering, vol. 128, No. 5, 2006, pp. 757-765.

Byrne, et al., "Early Experience in the Treatment of Intra-Cranial Aneurysms by Endovascular Flow Diversion: A Multicentre Prospective Study," PLoS One, vol. 5, No. 9, 2010, 8 pages.

Cagnazzo, et al., "Flow-Diversion Treatment of Unruptured Saccular Anterior Communicating Artery Aneurysms: A Systematic Review and Meta-Analysis," American Journal of Neuroradiology, vol. 40, No. 3, 2019, pp. 497-502.

Cagnazzo, et al., "Patency of the supraclinoid internal carotid artery branches after flow diversion treatment. A meta-analysis," Journal of Neuroradiology, vol. 46, 2019, pp. 9-14.

Cebral, et al., "Aneurysm Rupture Following Treatment with Flow-Diverting Stents: Computational Hemodynamics Analysis of Treatment," American Journal of Neuroradiology, vol. 32, 2011, pp. 27-33.

Cha & Pitt, "The biodegradability of polyester blends," Biomaterials, vol. 11, No. 2, 1990, pp. 108-112.

Collet, et al., "The Absorb bioresorbable vascular scaffold for the treatment of coronary artery disease," Expert Opinion on Drug Delivery, vol. 13, No. 10, 2016, pp. 1489-1499.

Connolly, et al., "Guidelines for the Management of Aneurysmal Subarachnoid Hemorrhage," Stroke, vol. 43, No. 6, 2012, pp. 1711-1737.

D'Souza, et al., "Biodegradable Stents—A New Era?," European Cardiology, vol. 4, No. 2, 2008, pp. 82-84.

Darsaut, et al., "Flow diverters failing to occlude experimental bifurcation or curved sidewall aneurysms: an in vivo study in canines," Journal of Neurosurgery, vol. 117, 2012, pp. 37-44.

De Vries, et al., "New Generation of Flow Diverter (Surpass) for Unruptured Intracranial Aneurysms," Stroke, vol. 44, No. 6, 2013, pp. 1567-1577.

Ding, et al., "Experimental testing of a new generation of flow diverters in sidewall aneurysms in rabbits," American Journal of Neuroradiology, vol. 36, No. 4, 2015, pp. 732-736.

Eddleman, et al., "Chapter 13: Intracranial Aneurysms," retrieved on Mar. 8, 2021, << https://neupsykey.com/intracranial-aneurysms-2/>> MediNeupsy Key, 2016, 8 pages.

Essbaiheen, et al., "Transient in-stent stenosis at mid-term angiographic follow-up in patients treated with SILK flow diverter stents: incidence, clinical significance and long-term follow-up," Journal of NeuroInterventional Surgery, vol. 11, No. 2, 2019, pp. 166-170.

Etminan & Rinkel, "Unruptured intracranial aneurysms: development, rupture and preventive management," Nature Reviews Neurology, vol. 12, No. 12, 2016, pp. 699-713.

(56) References Cited

OTHER PUBLICATIONS

Freeman, "Bioabsorbable stents for gastrointestinal endoscopy," Techniques in Gastrointestinal Endoscopy, vol. 3, No. 2, 2001, pp. 120-125.

Garcia, et al., "Influence of geometrical parameters on radial force during self-expanding stent deployment. Application for a variable radial stiffness stent," Journal of the Mechanical Behavior of Biomedical Materials, vol. 10, 2012, pp. 166-175.

Ginsberg, et al., "In vivo evaluation of a new bioabsorbable self-expanding biliary stent," Gastrointestinal Endoscopy, vol. 58, No. 5, 2003, pp. 777-784.

Goertz, et al., "Safety and efficacy of the Derivo Embolization Device for the treatment of ruptured intracranial aneurysms," Journal of NeuroInterventional Surgery, vol. 11, No. 3, 2019, pp. 290-295.

Gross & Frerichs, "Stent usage in the treatment of intracranial aneurysms: past, present and future," Journal of Neurology, Neurosurgery, and Psychiatry, vol. 84, No. 3, 2013, pp. 244-253.

Hampton, et al., "Mural destabilization after aneurysm treatment with a flow-diverting device: a report of two cases," Journal of NeuroInterventional Surgery, vol. 3, 2011, pp. 167-171.

Hong, et al., "Effects of metal coverage rate of flow diversion device on neointimal growth at side branch ostium and stented artery: an animal experiment in rabbit abdominal aorta," Neuroradiology, vol. 54, No. 8, 2012, pp. 849-855.

Kadirvel, et al., "Cellular Mechanisms of Aneurysm Occlusion after Treatment with a Flow Diverter," Radiology, vol. 270, No. 2, 2014, pp. 394-399.

Kang, et al., "Stent Thrombosis With Drug-Eluting Stents and Bioresorbable Scaffolds: Evidence From a Network Meta-Analysis of 147 Trials," JACC: Cardiovascular Interventions, vol. 9, No. 12, 2016, pp. 1203-1213.

Kangas, et al., "Comparison of strength properties of poly-L/D-lactide (PLDLA) 96/4 and polyglyconate (Maxon) sutures: in vitro, in the subcutis, and in the achilles tendon of rabbits," Journal of Biomedical Materials Research, vol. 58, No. 1, 2001, pp. 121-126.

Kim, et al., "Comparison of Two Stents in Modifying Cerebral Aneurysm Hemodynamics," Annals of Biomedical Engineering, vol. 36, No. 5, 2008, pp. 726-741.

Kim, et al., "Mechanical modeling of self-expandable stent fabricated using braiding technology," Journal of Biomechanics, vol. 41, 2008, pp. 3202-3212.

Kim, et al., "Stent Application for the Treatment of Cerebral Aneurysms," Neurointervention, vol. 6, No. 2, 2011, pp. 53-70.

Kiselev, et al., "Flow diversion versus parent artery occlusion with bypass in the treatment of complex intracranial aneurysms: Immediate and short-term outcomes of the randomized trial," Clinical Neurology and Neurosurgery, vol. 172, 2018, pp. 183-189.

Kojima, et al., "The study of flow diversion effects on aneurysm using multiple enterprise stents and two flow diverters," Asian Journal of Neurosurgery, vol. 7, No. 4, 2012, pp. 159-165.

Kolandaivelu, et al., "Stent Thrombogenicity Early in High-Risk Interventional Settings Is Driven by Stent Design and Deployment and Protected by Polymer-Drug Coatings," Circulation, vol. 123, No. 13, 2011, pp. 1400-1409.

Kossuth, et al., "Design Principles of Bioresorbable Polymeric Scaffolds," Interventional Cardiology Clinics, vol. 5, No. 3, 2016, pp. 349-355.

Kotsar, et al., "Biodegradable braided poly(lactic-co-glycolic acid) urethral stent combined with dutasteride in the treatment of acute urinary retention due to benign prostatic enlargement: a pilot study," BJU International, vol. 103, No. 5, 2009, pp. 626-629.

Kraus, et al., "Safety and efficacy of the Derivo Embolization Device for the treatment of unruptured intracranial aneurysms: a multicentric study," Journal of NeuroInterventional Surgery, vol. 11, No. 1, 2019, pp. 68-73.

Kulcsar, et al., "Intra-Aneurysmal Thrombosis as a Possible Cause of Delayed Aneurysm Rupture after Flow-Diversion Treatment," American Journal of Neuroradiology, vol. 32, No. 1, 2011, pp. 27-33.

Lamsa, et al., "Biocompatibility of a new bioabsorbable radiopaque stent material (BaSO4 containing poly-L,D-lactide) in the rat pancreas," Pancreatology, vol. 6, No. 4, 2006, pp. 301-305.

Liou & Li, "Effects of stent porosity on hemodynamics in a sidewall aneurysm model," Journal of Biomechanics, vol. 41, 2008, pp. 1174-1183.

Lubicz, et al., "Silk flow-diverter stent for the treatment of intracranial aneurysms: a series of 58 patients with emphasis on long-term results," American Journal of Neuroradiology, vol. 36, No. 3, 2015, pp. 542-546.

Malhotra, et al., "Comparative effectiveness analysis of Pipeline device versus coiling in unruptured aneurysms smaller than 10 mm," Journal of Neurosurgery, vol. 132, No. 1, 2019, pp. 42-50.

Mano, et al., "Natural origin biodegradable systems in tissue engineering and regenerative medicine: present status and some moving trends," Journal of the Royal Society Interface, vol. 4, 2007, pp. 999-1030.

Marosfoi, et al., "In situ tissue engineering: endothelial growth patterns as a function of flow diverter design," Journal of Neuroradiology, vol. 9, No. 10, 2017, pp. 994-998.

Maurice-Williams & Lafuente, "Intracranial aneurysm surgery and its future," Journal of The Royal Society of Medicine, vol. 96, No. 11, 2003, pp. 540-543.

Mohlenbruch, et al., "Multicenter Experience with FRED Jr Flow Re-Direction Endoluminal Device for Intracranial Aneurysms in Small Arteries," American Journal of Neuroradiology, vol. 38, No. 10, 2017, pp. 1959-1965.

Mori, et al., "Abstract 15796: Acute Thrombogenicity and Vascular Response After Bioresorbable Vascular Scaffold Implantation Evidenced From Porcine Coronary Model," Circulation, vol. 136, No. 1, 2017, 6 pages.

Muhl-Benninghaus, et al., "Transient in-stent stenosis: a common finding after flow diverter implantation," Journal of NeuroInterventional Surgery, vol. 11, 2019, pp. 196-199.

Mut, et al., "Association between hemodynamic conditions and occlusion times after flow diversion in cerebral aneurysms," Journal of NeuroInterventional Surgery, vol. 7, No. 4, 2015, pp. 286-290.

Nelson, et al., "The Pipeline Embolization Device for the Intracranial Treatment of Aneurysms Trial," American Journal of Neuroradiology, vol. 32, No. 1, 2011, pp. 34-40.

Nuutinen, et al., "Mechanical properties and in vitro degradation of bioresorbable knitted stents," Journal of Biomaterials Science, Polymer Edition, vol. 13, No. 12, 2002, pp. 1313-1323.

Nuutinen, et al., "Mechanical properties and in vitro degradation of bioabsorbable self-expanding braided stents," Journal of Biomaterials Science, Polymer Edition, vol. 14, No. 3, 2003, pp. 225-266.

Otsuka, et al., "The importance of the endothelium in atherothrombosis and coronary stenting," Nature Reviews Cardiology, vol. 9, No. 8, 2012, pp. 439-453.

Phenox, "The Power of safety and security. Complete deployment with full recoverability," retrieved on Mar. 8, 2021, <<https://phenox.net/international/p64-flow-modulation-device/>> Phenox, 2021, 3 pages.

Pumar, et al., "Preliminary Experience with Leo Self-Expanding Stent for the Treatment of Intracranial Aneurysms," American Journal of Neuroradiology, vol. 26, No. 19, 2005, pp. 2573-2577.

Raber, et al., "Very Late Scaffold Thrombosis," Journal of the American College of Cardiology, vol. 66, No. 7, 2015, pp. 1901-1914.

Rebelo, et al., "Influence of design parameters on the mechanical behavior and porosity of braided fibrous stents," Material and Design, vol. 86, 2015, pp. 237-247.

Ringer & Kilburg, "Aneurysm embolization: coiling, stenting, flow diversion," retrieved on Mar. 8, 2021, <<https://mayfieldclinic.com/pe-coiling.htm>> Mayfield Brain & Spine, vol. 1, 2020, 6 pages.

Ringer & Kilburg, "Aneurysm surgery: clipping," retrieved on Mar. 8, 2021, <<https://mayfieldclinic.com/pe-clipping.htm#:~:text=The%20brain%20is%20gently%20retracted,applied%20to%20open%20the%20blades.>> Mayfield Brain & Spine, vol. 1, 2020, 4 pages.

Sadasivan, et al., "An Original Flow Diversion Device for the Treatment of Intracranial Aneurysms," Stroke, vol. 40, No. 3, 2009, pp. 952-958.

(56) References Cited

OTHER PUBLICATIONS

Sanai, et al., "Bypass surgery for complex brain aneurysms: an assessment of intracranial-intracranial bypass," Neurosurgery, vol. 65, No. 4, 2009, pp. 670-683.
Schievink, "Intracranial Aneurysms," New England Journal of Medicine, vol. 336, 1997, pp. 28-40.
Seshadhri, et al., "Impact of stents and flow diverters on hemodynamics in idealized aneurysm models," Journal of Biomechanical Engineering, vol. 133, 2011, 9 pages.
Sharma, et al., "The development of bioresorbable composite polymeric implants with high mechanical strength," Nature Materials, vol. 17, 2018, pp. 96-103.
Sotomi, et al., "Bioresorbable Scaffold The Emerging Reality and Future Directions," Circulation Research, vol. 120, No. 8, 2017, pp. 1341-1352.
Suuronen, et al., "A 5-year in vitro and in vivo study of the biodegradation of polylactide plates," Journal of Oral and Maxillofacial Surgery, vol. 56, No. 5, 1998, pp. 604-614.
Tahtinen, et al., "The silk flow-diverting stent in the endovascular treatment of complex intracranial aneurysms: technical aspects and midterm results in 24 consecutive patients," Neurosurgery, vol. 70, No. 3, 2012, pp. 617-623.
Tang, et al., "The effects of stent porosity on the endovascular treatment of intracranial aneurysms located near a bifurcation," Journal of Biomedical Science and Engineering, vol. 6, 2013, pp. 812-822.
Toth & Cerejo, "Intracranial aneurysms: Review of current science and management," Vascular Medicine, vol. 23, No. 3, 2018, pp. 276-288.
U.S. Food and Drug Administration, "FDA Investigating Increased Rate of Major Adverse Cardiac Events Observed in Patients Receiving Abbott Vasculars Absorb GT1 Bioresorbable Vascular Scaffold (BVS)—Letter to Health Care Providers," 2017, 2 pages.
Vert, et al., "Bioresorbability and biocompatibility of aliphatic polyesters," Journal of Materials Science: Materials in Medicine, vol. 3, 1992, pp. 432-446.
Waksman, et al., "Comparison of Acute Thrombogenicity for Metallic and Polymeric Bioabsorbable Scaffolds: Magmaris Versus Absorb in a Porcine Arteriovenous Shunt Model," Circulation: Cardiovascular Interventions, vol. 10, No. 8, 2017, 10 pages.
Wang, et al., "Biodegradable flow-diverting device for the treatment of intracranial aneurysm: short-term results of a rabbit experiment," Neuroradiology, vol. 55, No. 5, 2013, pp. 621-628.
Wang, et al., "Flow diverter effect of LVIS stent on cerebral aneurysm hemodynamics: a comparison with Enterprise stents and the Pipeline device," Journal of Translational Medicine, vol. 14, 2016, 10 pages.
Wedro, "Brain Aneurysm (Cerebral Aneurysm)," retrieved on Mar. 8, 2021, <<https://www.medicinenet.com/brain_aneurysm/article.htm>> MedicineNet, 2019, 8 pages.
Wong, "Minimum Headache Duration Prompting Subarachnoid Hemorrhage Workup," retrieved on Mar. 8, 2021, <<https://www.neurologyadvisor.com/topics/migraine-and-headache/minimum-headache-duration-prompting-subarachnoid-hemorrhage-workup>> Neurology Advisor, 2017, 5 pages.
Yu, et al., "Hemodynamic study for new stent design with mesh-typed stents in a cerebral aneurysm model using PIV," 12th International Conference on Control, Automation and Systems, 2012, pp. 1706-1709.
Zhang, et al., "Towards optimal flow diverter porosity for the treatment of intracranial aneurysm," Journal of Biomechanics, vol. 82, 2019, pp. 20-27.
Decision to Grant for Japanese Application No. JP20200572587 dated May 7, 2024, 8 pages w/ English translation.
EP 19767040.9, Extended European Search Report dated Nov. 16, 2021, 9 pages.
Jabbour, Pascal M., "Biomechanics of Cerebral Aneurysms". Neurovascular Surgical Techniques. 2013. pp. 207-211, 9 pages.
Non-Final Office Action for U.S. Appl. No. 18/336,241 dated Nov. 9, 2023, 28 pages.
Office Action dated Aug. 25, 2023 for EP Application No. 19767040.9, 3 pages.
Office Action dated Jul. 5, 2023 for EP Application No. 19767040.9, 4 pages.
Office Action for India Application No. IN202027044123 dated Jun. 20, 2024, 3 pages.
Office Action for India Application No. IN202027044123 dated Apr. 22, 2024, 3 pages.
Office Action for India Application No. IN202027044123 dated Mar. 14, 2024, 3 pages.
Office Action for India Application No. IN202027044123 dated May 24, 2024, 3 pages.
Office Action for Japan Application No. 2020-572587 dated Aug. 25, 2023, 10 pages w/ English translation.
Office Action for Japan Application No. 2020-572587 dated Feb. 14, 2023, 10 pages w/ English translation.
PCT/CA2019/050304, International Preliminary Report on Patentability dated Sep. 15, 2020, 7 pages.
PCT/CA2019/050304, International Search Report and Written Opinion of the International Searching Authority dated Jun. 12, 2019, 9 pages.
Restriction Requirement for U.S. Appl. No. 18/336,241 dated Aug. 18, 2023, 7 pages.
Office Action dated Apr. 8, 2025 for Japan Application No. 2024-029588, 6 pages with English translation.
Restriction Requirement for U.S. Appl. No. 17/738,277 dated Apr. 17, 2025, 7 pages.

* cited by examiner

BIOABSORBABLE FLOW DIVERTING SCAFFOLD

CROSS REFERENCE TO RELATED APPLICATIONS

This application is a continuation of International Patent Application No. PCT/CA2019/050304, filed Mar. 12, 2019, which claims priority to U.S. Provisional Patent Application No. 62/641,891 filed Mar. 12, 2018, the contents of both of which are incorporated herein by reference in their entirety.

FIELD OF THE INVENTION

This disclosure relates to scaffolds made of a braid of bioabsorbable polymeric fibers for implantation within a lumen of a mammalian body. Particular aspects of this disclosure relate scaffolds made from such braids that are configured to divert blood flow from a pathology associated with a blood vessel.

DESCRIPTION OF RELATED ART

There is an abundance of medical devices that are known in the art, which are implanted into blood vessels in the body to treat various pathologies. For example, an aneurysm is an outward bulging, balloon-like structure caused by a localized weak spot on a blood vessel wall. Aneurysms have thin, weak walls and are thus at risk of rupturing. "Flow-diverting" scaffolds have been proposed to treat aneurysms, by which a stent is inserted to span the neck of an aneurysm in order to divert flow past the aneurysm and thus allow it to heal. Flow diversion thus removes the need to enter an aneurysm. Such flow-diverting scaffolds are described in, for example, U.S. Pat. Nos. 8,715,312 and 8,267,986, 8,715,312 and 8,267,986 describe scaffolds made of braided metal wires. The Pipeline™ Flex embolization device (Medtronic), is used for endovascular treatment of large or giant wide-necked intracranial aneurysms. The Pipeline™ Flex device consists of 75% cobalt chromium/25% platinum tungsten wires.

The metal composition of the flow-diverting scaffolds known in the art provides disadvantages. As they are permanent and cannot be removed, they present various drawbacks, including risk of thrombosis that requires patients to remain anti-platelet medications long-term, risk of hyperplasia, prevention of vascular lumen remodeling or expansion, and occlusion of the blood vessel. Metal scaffolds are also present disadvantages in the context of CT and MRI imaging post-implantation as the signal they reflect tends to be too bright.

Accordingly, there is a need for implantable devices that eliminate or reduce the negative responses of the body at the implantation site while allowing for the prevention or treatment of a disease. Bioresorbable scaffolds have advantages compared to the metal scaffolds; including non-permanency. However, clinical studies showed that bioabsorbable coronary have higher risks of thrombosis (Masayuki et al., *Circulation* 136, A15796-A15796; Räber et al., *ACC* (*Journal Am. Coll. Cardiol.* 66, 1901-1914; Kang et al., *ACC Cardiovasc. Interv.* 9, 1203-1212). Furthermore, Waksmen et al. (*Circ. Cardiovasc. Interv.* 10, e004762) have demonstrated the higher thrombogenicity of scaffolds made with the bioabsorbable polymer nature of PLLA.

SUMMARY OF THE INVENTION

Other aspects and features of the present invention will become apparent to those ordinarily skilled in the art upon review of the following description of specific embodiments of the invention in conjunction with the accompanying figures.

Aspects of the disclosure relate to a device comprising a resiliently deformable tubular body for positioning in a body lumen defined by a body wall, the tubular body comprising a braid of interwoven bioabsorbable polymeric fibers, wherein the tubular body comprises at least 38 polymeric fibers. In various embodiments; when the device is in an expanded formation; the braid has a porosity in the range of about 5% to about 80%. In various embodiments, when the device is in an expanded formation; the braid has a porosity in the range of about 60% to about 80%.

Aspects of the disclosure relate to a device comprising a resiliently deformable tubular body for positioning in a body lumen defined by a body wall, the tubular body comprising a braid of interwoven bioabsorbable polymeric fibers, wherein, when the device is in an expanded formation, the braid has a porosity in the range of about 60% to about 80%. In various embodiments; the tubular body comprises at least 38 polymeric fibers.

In various embodiments of the devices described above, the braid comprises 38 to 96 bioabsorbable polymeric fibers. In various embodiments, the braid comprises at least 44 bioabsorbable polymeric fibers. In various embodiments, the braid comprises at least 46 bioabsorbable polymeric fibers. In various embodiments, the braid comprises at least 48 bioabsorbable polymeric fibers. In various embodiments; the braid comprises at least 72 bioabsorbable polymeric fibers. In various embodiments, the braid comprises 44 bioabsorbable polymeric fibers. In various embodiments; the braid comprises 46 bioabsorbable polymeric fibers. In various embodiments, the braid comprises 48 bioabsorbable polymeric fibers. In various embodiments; wherein the braid comprises 72 bioabsorbable polymeric fibers. In various embodiments, the braid comprises at least 96 bioabsorbable polymeric fibers.

In various embodiments of the devices described above; the bioabsorbable polymeric fibers have a diameter of at least about 30 μm. In various embodiments, the bioabsorbable polymeric fibers have a diameter in the range of about 30 μm to about 80 μm. In various embodiments; the bioabsorbable polymeric fibers have a diameter of about 40 μm. In various embodiments; bioabsorbable polymeric fibers have a diameter of about 50 μm. In various embodiments; the bioabsorbable have a diameter of about 60 μm. In various embodiments; the bioabsorbable polymeric fibers have a diameter of about 70 μm. In various embodiments, the bioabsorbable polymeric fibers have a diameter of about 80 μm.

In various embodiments of the devices described above; the bioabsorbable polymeric fibers are interwoven in a 2-under-2-over-2 pattern. In various embodiments, the bioabsorbable polymeric fibers are interwoven in a 1-overr-2-under-2 pattern. In various embodiments, the bioabsorbable polymeric fibers are interwoven in 1-over-1-under-1 pattern.

In various embodiments of the devices described above, the diameter of the tubular body is about 4 mm. In various embodiments, the bioabsorbable polymeric fibers are interwoven at a pitch angle of about 16° or less. In various embodiments, the bioabsorbable polymeric fibers are interwoven at a pitch angle of about 14° or less.

In various embodiments of the devices described above, the diameter of the tubular body is about 5 mm. In various embodiments, the bioabsorbable polymeric fibers are interwoven at a pitch angle of about 12° or less. In various embodiments, the bioabsorbable polymeric fibers are interwoven at a pitch angle of about 10° or less.

In various embodiments of the devices described above, the diameter of the tubular body is about 3 mm. In various embodiments, the bioabsorbable polymeric fibers are interwoven at a pitch angle of about 18° or less. In various embodiments, the bioabsorbable polymeric fibers are interwoven at a pitch angle of about 16° or less.

In various embodiments of the devices described above, the diameter of the tubular body is about 7 mm. In various embodiments, the bioabsorbable polymeric fibers are interwoven at a pitch angle of about 9° or less.

In various embodiments of the devices described above, when the device is in an expanded formation the braid has a pore density of in the range of about 10 pores/mm2 to about 32 pores/mm2.

In various embodiments of the devices described above; the tubular body further comprises a visualization aid. In various embodiments, the visualization aid comprises a radio-opaque material. In various embodiments; the radio opaque material comprises iodine or barium. In various embodiments, the visualization aid comprises at least one wire comprising a radio-opaque material, wherein each wire is interwoven with the plurality of bioabsorbable polymeric fibers to form part of the braid.

In various embodiments of the devices described above; the tubular body comprises means for facilitating and/or maintaining radial and/or axial expansion of the tubular body in the body lumen. In various embodiments, the means for facilitating and maintaining expansion of the tubular body in the body lumen is at least one wire, wherein each wire is interwoven with the plurality of bioabsorbable polymeric fibers to form part of the braid. In various embodiments, the at least one wire comprises a radio opaque material.

In various embodiments of the devices described above; the at least one wire is a resiliently deformable wire. In various embodiments; the resiliently deformable wire comprises a nickel-titanium alloy or a cobalt-chromium-nickel alloy. In various embodiments, each wire independently comprises: a nickel-titanium alloy coated with the radio-opaque material; a drawn filled tube (DFT) comprising a nickel-titanium alloy exterior and a core comprising the radio-opaque material; a DFT comprising an exterior comprising the radio-opaque material and a core comprising a nickel-titanium alloy; a cobalt-chromium-nickel alloy coated with the radio-opaque material; a (DFT) comprising a cobalt-chromium-nickel alloy exterior and a core comprising the radio-opaque material; or a DFT comprising an exterior comprising the radio-opaque material and a core comprising cobalt-chromium-nickel alloy.

In various embodiments of the devices described above, the radio-opaque material comprises iodine or barium.

In various embodiments of the devices described above, the radio-opaque material comprises a radio-opaque metal. In various embodiments, the radio-opaque metal is tantalum; gold; platinum, or a combination thereof.

In various embodiments of the devices described above; the at least one wire comprises a tantalum-coated nitinol wire.

In various embodiments of the devices described above; the at least one wire comprises a DFT comprising a nitinol exterior and a platinum core.

In various embodiments of the devices described above, the at least one wire comprises 2 wires, 3 wires, 4 wires, 5 wires; 6 wires, 7 wires, 8 wires; 9 wires, or 10 wires.

In various embodiments of the devices described above, the plurality of polymeric fibers comprise polylactides (PLA), polyglycolides (PGA); polycaprolactone (PCL), polylactide-co-glycolides (PLGA), polyanhydrides, polyorthoesters, poly(N-(2-hydroxypropyl) methacrylamide); poly(I-aspartamide), DLPLA-poly(dl-lactide); poly (L-Lactic acid); LPLA-poly(I-lactide); PDO-poly (dioxanone), PGA-TMC-poly (polyglycolide-co-trimethylene carbonate); PGA-LPLA-poly(1-lactide-co-glycolide), PGA-DLPLA-poly(dl-lactide-co-glycolide), LPLA-DLPLA-poly(I-lactide-co-dl-lactide), PDO-PGA-TMC-poly(glycolide-co-trimethylene carbonate-co-dioxanone), or any combination thereof. In various embodiments, the plurality of polymeric fiber comprise polylactides (PLA), polylactide-co-glycolides (PLGA), DLPLA-poly(dl-lactide), poly-L-Lactic acid), LPLA-poly(I-lactide), PGA-LPLA-poly(I-lactide-co-glycolide), PGA-DLPLA-poly(dl-lactide-co-glycolide), LPLA-DLPLA-poly(I-lactide-co-dl-lactide), or any combination thereof. In various embodiments, the plurality of polymeric fibers comprise poly-L-lactic acid (PLLA).

In various embodiments of the devices described above, the tubular body comprises a therapeutic agent conjugated to the bioabsorbable polymeric fibers. In various embodiments, the bioabsorbable polymeric fibers are coated with a therapeutic agent. In various embodiments, the therapeutic agent is an antibiotic agent, an antiviral agent, an analgesic, a muscle relaxant, a chemotherapeutic agent, an intra-arterial vasodilating agent, a calcium channel inhibitor, a calcium channel antagonist, a calcium channel blocker, a transient receptor potential protein blocker, an endothelin antagonist, a blood thinning agent, an antiplatelet agent, or any combination thereof. In various embodiments, the therapeutic agent is aspirin, heparin, Ticagrelor, 5-fluorouracil, melphalan, or clopidogrel. In various embodiments, the therapeutic agent is paclitaxel, sirolimus, everolimus, temozolamide, cyclophosphamide, doxorubicin, irinotecan, azathioprine, methotrexate, cisplatin, or vincristine.

In various embodiments of the devices described above, the lumen is the lumen of a blood vessel. In various embodiments, the blood vessel is an intracranial vessel. In various embodiments, the device is for positioning adjacent to a pathology of the blood vessel to divert blood flow from the pathology. In various embodiments, the pathology is an aneurysm, a cancer, an infection, coronary artery disease, carotid artery atherosclerotic disease, or intracranial atherosclerosis.

In various embodiments of the devices described above, the device is for positioning in the lumen at a site adjacent to a pathology of or proximal to the body wall to supply lactic acid to the site.

Aspects of the disclosure relate to use of a device as defined above for deployment within a lumen of a body to treat a pathology of or proximal to a body wall defining the lumen. Aspects of the disclosure relate to use of a device as defined above for deployment within a body lumen to deliver a therapeutic agent to a pathology of or proximal to a body wall defining the lumen. Aspects of the disclosure relate to use of a device as defined above for deployment within a body lumen to deliver lactic acid to a site proximal to a pathology of or proximal to a body wall defining the lumen. In various embodiments, the body wall is the wall of a blood vessel. In various embodiments, the blood vessel is an intracranial blood vessel. In various embodiments, the pathology is an aneurysm, a cancer, an infection, coronary artery disease, carotid artery atherosclerotic disease, or intracranial atherosclerosis Aspects of the disclosure relate to a method of treating a pathology of or proximal to a body wall, the method comprising deploying a device as defined in above in a lumen defined by the body wall at a position proximal to the pathology. Aspects of the disclosure relate to a method of delivering lactic acid to a site proximal to a pathology of, or proximal to, a body wall, the method comprising deploying a device as described above within a lumen defined by the body wall at the site proximal to the pathology. In various embodiments, the body wall is the wall of a blood vessel. In various embodiments, the blood vessel is an intracranial blood vessel. In various embodiments, the pathology is an aneurysm, a cancer, an infection, coronary artery disease, carotid artery atherosclerotic disease, or intracranial atherosclerosis.

BRIEF DESCRIPTION OF THE DRAWINGS

In drawings which illustrate embodiments of the invention.

Definitions

Figure 1:
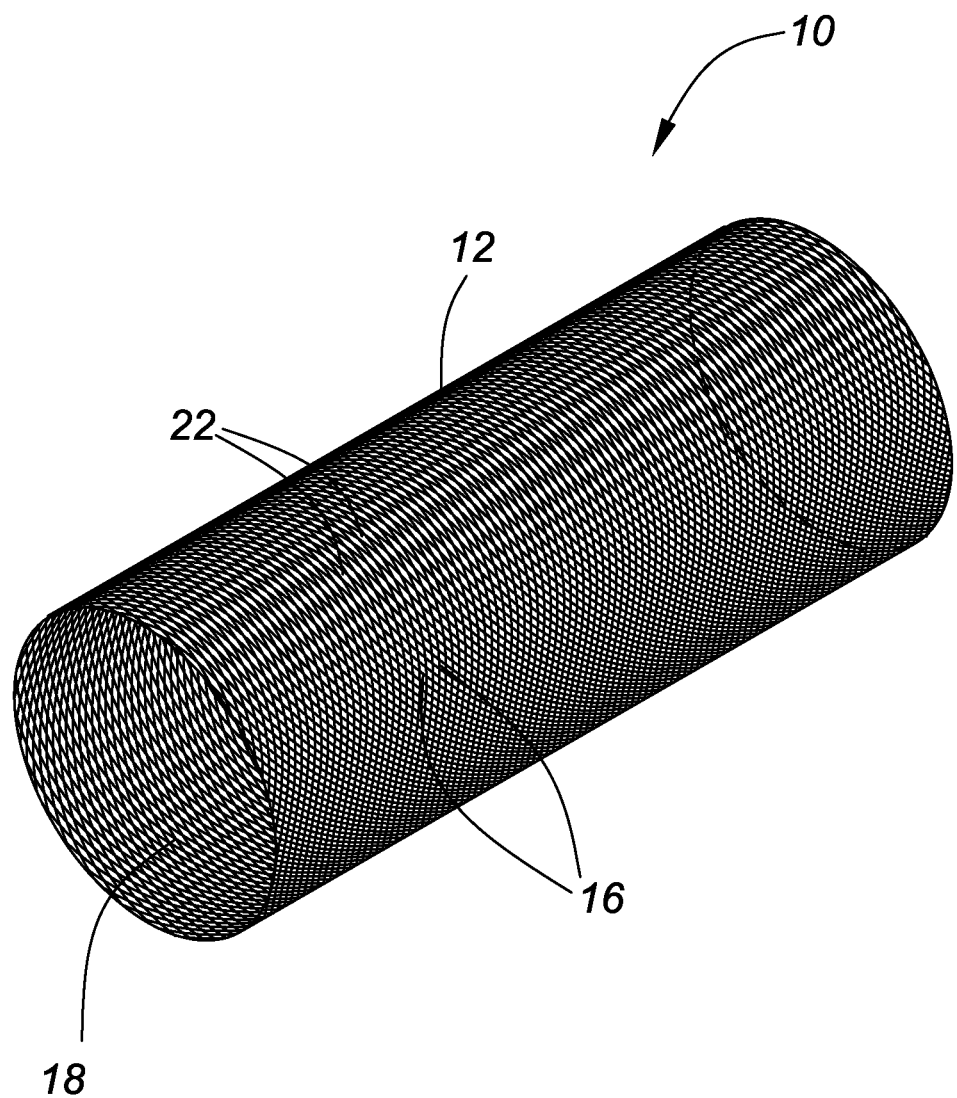
FIG. 1 is an isometric view of an implantable device comprising a braid of interwoven bioasbsorbable polymeric fibers according to a first embodiment.

"Pathology" as used herein refers to the structural and functional deviations from the normal that constitutes or characterizes a disease, condition, or disorder.

"Comprising" as used herein means "including, but not limited to".

"Consisting" as used herein means "including and limited to".

"Drug" or "therapeutic agent" as used herein can refer to any of a variety of drugs, pharmaceutical compounds, other bioactive agent that can be used as active agents to prevent or treat a disease.

"Bioabsorbable", "biodegradable", and "bioresorbable" are used herein synonymously to refer to a material or structure that degrades or dissolves in living tissues or systems of a body over time.

"Body lumen" as used herein refers to the cavity defined by a tubular structure of a mammalian body including, but not limited to, a blood vessel, a ureter, a urethra, a bile duct.

"Wall" as used herein refers to tissue that forms a tubular structure of a mammalian body including, but not limited to, a blood vessel wall, a ureter wall, a urethra wall, a bile duct wall.

"Scaffold" as used herein refers to a tubular structure that may be inserted into a body lumen. Scaffolds include stents that can insert into a blocked passageway to keep them open and restore the flow of blood or other fluids. Scaffolds also include devices that are not primarily intended to keep a blocked passageway open, but rather intended to divert flow of fluids. Scaffolds may also serve as a support for tissue growth such as neointimal growth. Scaffolds may also serve as a platform for the delivery of therapeutic agents. Scaffolds may be made of either metal or plastic.

"Visualization aid" as used herein refers to any structure that facilitates imaging by x-ray fluoroscopy.

"Resiliently deformable" as used herein pertains to an object that is capable of autonomously returning to its original shape upon release from a bent, stretched, compressed, or otherwise deformed shape.

"Endovascular device" as used herein refers to a prosthesis that can be implanted within a body lumen or body conduit.

"Fiber" as used herein refers to a filament, thread, tendril, or strand from which a textile is formed.

"Polymeric fiber" as used herein refers to fibers comprising a series of repeating monomeric units that have been cross-linked or polymerized. In some embodiments disclosed herein, only one polymer is used. In another embodiment, a combination of two or more polymers may be used. In another embodiment, polymers may be used with radio-opaque materials. The polymers and the combinations of polymers can be used in varying ratios to provide different properties. Polymers that may be used in the present invention include, for example, stable polymers, biostable polymers, durable polymers, inert polymers, organic polymers, organic-inorganic copolymers or inorganic polymers. Suitable polymers are bioabsorbable, biocompatible, bioresorbable, resorbable, degradable, and biodegradable polymers.

"Flow-diversion" as used herein refers to diversion of bodily fluid flow away from a pathology.

"Porosity" as used herein is, for a device in its fully expanded formation, the ratio of the free area to the total area, where the free area is equal to the total area minus the material surface area. In other words, the percentage of the overall device wall surface area that is open and fiber-free.

DETAILED DESCRIPTION

This disclosure generally relates to implantable devices, methods for manufacture and uses in either the prophylaxis or treatment of a pathology. Any term or expression not expressly defined herein shall have its commonly accepted definition understood by a person skilled in the art. To the extent that the following description is of a specific embodiment or a particular use of the invention, it is intended to be illustrative only, and not limiting of the invention, which should be given the broadest interpretation consistent with the description as a whole and with the claims.

Figure 2:
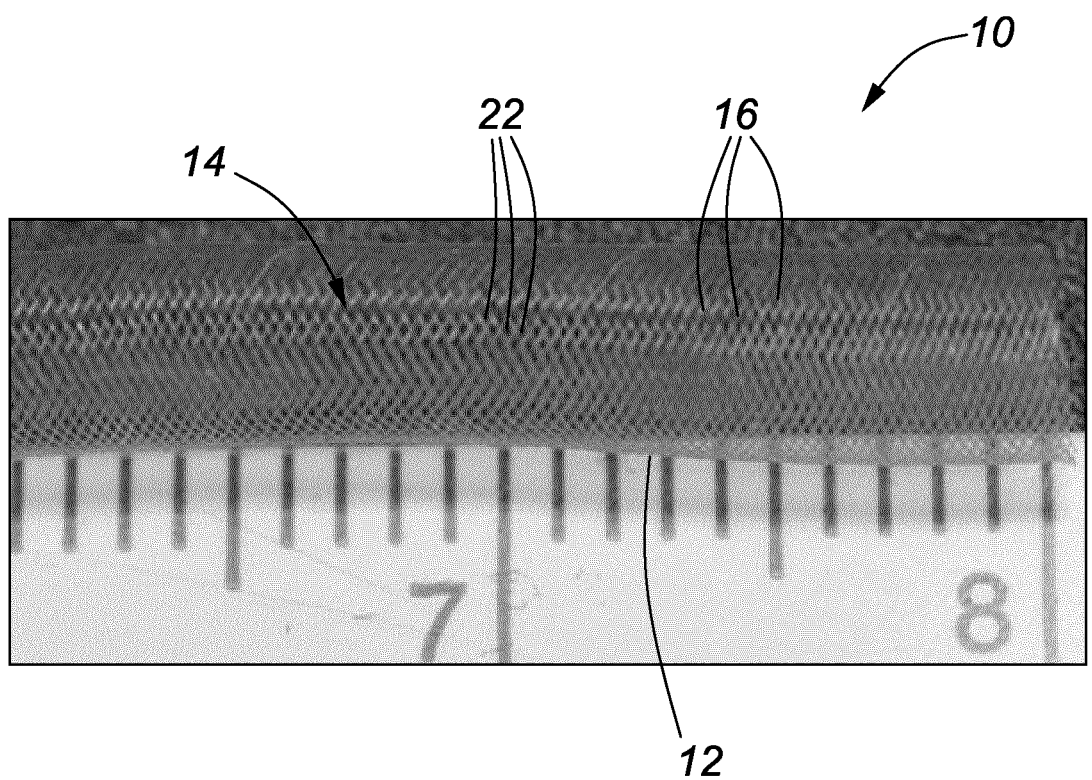
FIG. 2 is a picture of an embodiment of an implantable endovascular device comprising 48 interwoven poly L-lactic acid (PLLA) polymeric fibers.

Referring to FIGS. 1 and 2, a device for positioning with a body lumen to achieve flow diversion of a bodily fluid according to a first embodiment of the invention is shown generally at 10. Referring to FIG. 2, device 10 comprises a resiliently deformable tubular body 12 formed of a braid 14 of interwoven bioabsorbable polymeric fibers 16. Referring to FIG. 1, tubular body 12 defines a lumen 18 through which a bodily fluid can continue to flow when device 10 is deployed within a body lumen. Overlapping bioabsorbable polymeric fibers 16 define pores 22.

In the presently described embodiment, braid 14 consists of 48 bioabsorbable polymeric fibers. However, flow diversion may be achieved with braids consisting of as few as 38 bioabsorbable polymeric fibers and as many as 96 bioabsorbable polymeric fibers. In various embodiments of the presently disclosed devices that are useful for flow diversion, a braid may comprise 40, 42, 44, 46, 48, 50, 52, 54, 56, 58, 60, 62, 64, 66, 68, 70, 72, 74, 76, 78, 80, 82, 84, 86; 88, 90, 92; or 94 bioabsorbable polymeric fibers. In particular embodiments of the presently disclosed devices that are useful for flow diversion, a braid may consist of 40, 42, 44, 46, 48, 50; 52, 54, 56, 58, 60, 62, 64, 66, 68, 70, 72, 74, 76, 78, 80, 82, 84, 86, 88, 90, 92, or 94 bioabsorbable polymeric fibers.

For applications where flow diversion is not necessary or desired; the braid of the presently disclosed invention could include as few as 20 bioabsorbable polymeric fibers; as few as 18 bioabsorbable polymeric fibers; as few as 16 bioabsorbable polymeric fibers, as few as 14 bioabsorbable polymeric fibers; or as few as 12 bioabsorbable polymeric fibers.

In the presently described embodiment; braid 14 consists of bioabsorbable polymeric fibers 16 having a diameter of 50 µm. Bioabsorbable polymeric fibers useful for the production of devices useful for flow diversion as disclosed herein will have a diameter of at least about 30 µm, and will generally have a diameter in the range of about 30 µm to about 80 µm. In various embodiments of the presently disclosed devices that are useful for flow diversion, the bioabsorbable polymeric fibers will have a diameter of about 30 µm, about 40 µm, about 50 µm, about 60 µm, about 70 µm, or about 80 µm. The skilled person will understand that bioabsorbable polymeric fibers with any diameter within this range may be useful in the production of a flow-diverting device.

For a flow diverting device; it is desirable for the tubular body to have a high flexibility so that it can be delivered through a microcatheter and, in various applications, through tortuous blood vessels and into the intracranial circulation. Accordingly, the upper limit of the diameter of the bioabsorbable polymeric fibers will be dictated by the desired flexibility of the tubular body as well as the diameter of the lumen into which the device is to be deployed.

Figure 3:
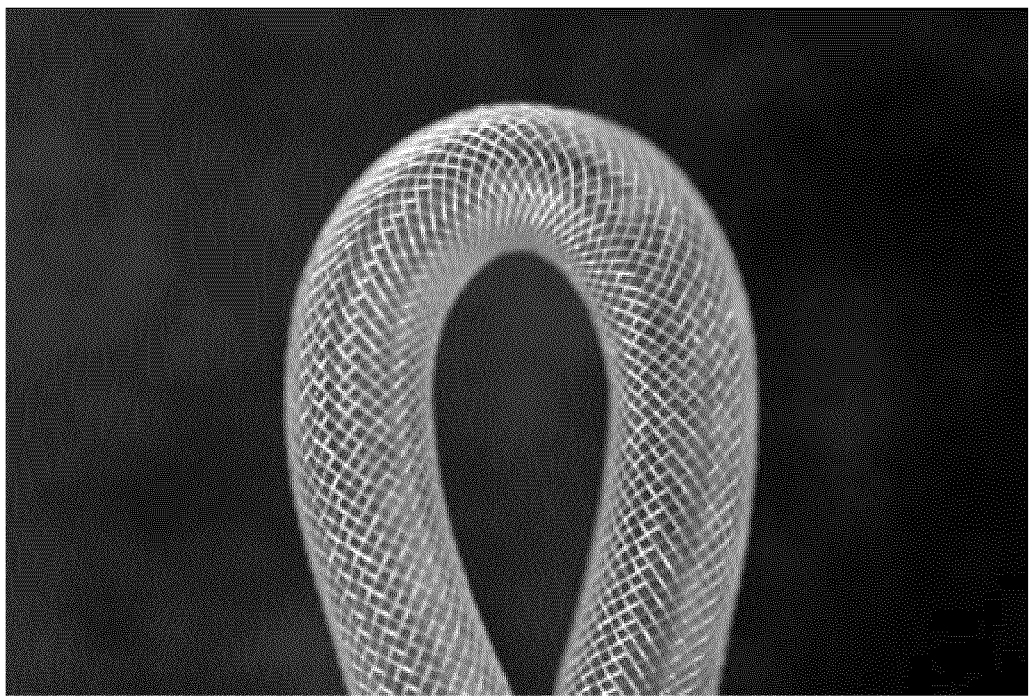
FIG. 3 is a picture of an embodiment of an implantable endovascular device comprising 48 interwoven poly L-lactic acid (PLLA) polymeric fibers showing the resilient deformability of the device.

FIG. 3 is a picture demonstrating the flexibility and resilient deformability of the device consisting of 48 poly-L-lactic acid (PLLA) bioabsorbable fibers.

Porosity

The braided nature of the device is essential to flow diversion applications. The braid allows for the manufacture of a tubular body with a sufficiently high material surface area/sufficiently low porosity to prevent significant lateral flow of fluid through the side of the tubular body; thereby by allowing it to divert flow of fluid away from any site of interest that is spanned by the device. The braid also allows for collapsibility of the device within a microcatheter for delivery. Furthermore; the bioabsorbable polymeric fibers slide against each other, thereby facilitating expansion and retraction of the tubular body.

For flow diversion applications, porosity is the one of the most important design factors. Lower porosities result in a lower inlet and outlet velocity of blood flow into an aneurysm sac; thereby increasing the chance of thrombosis and faster occlusion. Decreasing the porosity of a BW stent also decreases wall shear stress (WSS) on both aneurysm and parent arterial wall. On the other hand, pressure in the dome of the aneurysm sac rises with decreasing porosity; thereby increasing the risk of aneurysm rupture associated with flow diverting scaffolds currently in clinical trials.

For flow diversion applications, a porosity of the tubular body in the range of about 60% to about 80% is desirable. In preferred embodiments, the porosity is in the range of about 60% to about 70% In various embodiments of the devices disclosed herein, the porosity will be about 60%, about 65%, about 70%, about 75%, or about 80%. In various embodiments, a pore density in the range of 10 pores/mm2 to about 32 pores/mm2 is desirable. In particular embodiments, the pore density is about 18 pores/mm2. The skilled person will understand that as the porosity of the tubular body decreases; the flexibility/deformability of the tubular body may decrease. Accordingly, the limit to which porosity may be lowered is also informed by the required flexibility of the tubular body.

Pitch Angle

Figure 4:
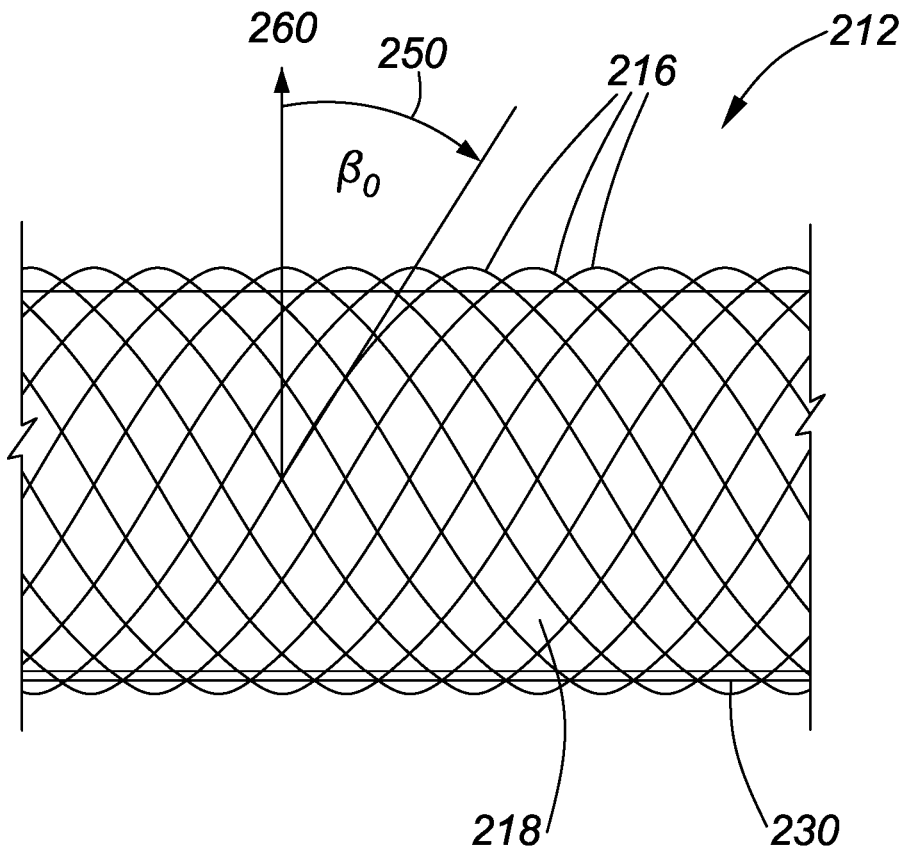
FIG. 4 is a schematic diagram of an implantable device comprising a braid of interwoven fibers that illustrates pitch angle.

The pitch angle of the braiding process is an important factor influencing the material surface area and porosity of the tubular body in its expanded formation, and thus a device's flow diversion capability. The pitch angle further influences the resiliency of the device to deformation and thus self-expandability. Referring to FIG. 4, a resiliently deformable tubular body of a device according to an embodiment of the disclosure is shown generally at 212. Tubular body 212 comprises a plurality of bioabsorbable polymeric fibers 216. Overlapping bioabsorbable polymeric fibers 216 define pores 218. Tubular body 212 is depicted on a mandrel 230 as the braid is being manufactured. Pitch angle 250 of the braid is the angle formed between a bioabsorbable polymeric fiber 216 and the transverse axis 260 of tubular body 212.

Figure 5:
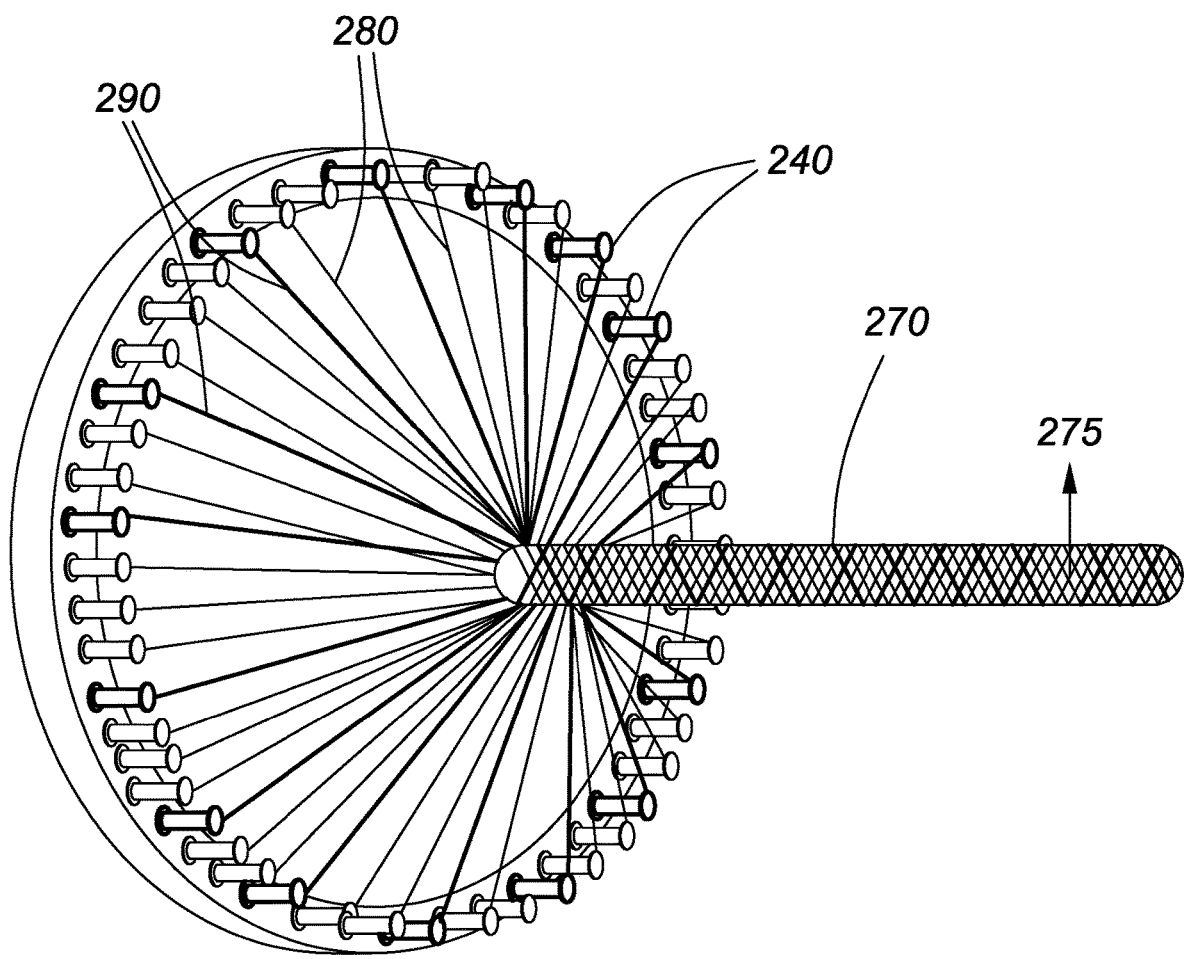
FIG. 5 is a schematic diagram of a braiding machine useful for manufacturing devices of the present disclosure.

Referring, to FIG. 5, the pitch angle 260 of the braid is effectively determined by the angle formed between the bioabsorbable fibers 280 as they extend from carriers 240 to mandrel 250 and the transverse axis 270 of the mandrel 250.

The pitch angle; tubular body diameter factor, and bioabsorbable polymeric fiber diameter factor together to influence porosity of the tubular body and thus the ability of a device to divert flow. Accordingly; it is necessary to adjust these variables depending on the bioabsorbable polymeric fibers to be used or the tubular body diameter in order to achieve a porosity in the range of typical flow diverting device. For example, for a bioabsorbable polymeric fiber having a diameter of 50 μm and a desired tubular body diameter of 4 mm, the pitch angle should be about 16° or less; or about 15° or less. For a desired tubular body diameter of 5 mm, the pitch angle should be about 12° or less; or about 11° or less. For a desired tubular body diameter of 3 mm, the pitch angle should be about 18° or less; or about 17° or less. For a desired tubular body diameter of 7 mm, the pitch angle should be about 9° or less. Table 1 below provides general guidance on suitable combinations of tubular body diameter, fiber diameter, and pitch angle. However, the skilled person will understand that the combinations indicated are not intended to be limiting, and that it would be well within the purview of a skilled person to adjust each factor accordingly to achieve a suitable porosity.

TABLE 1

Suggested parameters for flow diverting devices of the disclosure.

| Tubular Body Diameter (mm) | Bioabsorbable Polymeric Fiber Diameter (μm) | Pitch angle (gradian) |
| --- | --- | --- |
| 3 | 40 | 16 |
|   | 50 | 17-18 |
| 4 | 40 | 14 |
|   | 50 | 15-16 |
| 5 | 40 | 10 |
|   | 50 | 11-12 |

An achievable pitch angle is also dependent on the quality of the polymer fibers since it pitch angle imparts tension on the fibers that can potentially cause them to break. In general; a lower pitch angle allows for reduced porosity and a higher material surface area. By adding more fibers of a lower diameter, a lower pitch angle, and thus lower porosity, could be achieved for the device.

Bioabsorbable Polymeric Fibers

The polymer fibers used in the production of the disclosed devices comprise polymer material that is bioabsorbable. The polymeric material degrades in the body at a controlled/ predictable rate and known period of time. The rate of degradation may depend on the polymer material, the diameter of the bioabsorbable polymeric fiber, physiological conditions, the porosity of the tubular body; etc.

Referring back to FIG. 2; the bioabsorbable polymeric fibers 16 of the depicted embodiment comprise poly-L-lactic acid (PLLA). However, any one or more of a plurality of bioabsorbable polymeric fibers could be utilized including fibers comprising polylactides (PLA), Polyglycolides (PGA), polycaprolactone (PCL); polylactide-co-glycolides (PLGA), polyanhydrides, polyorthoesters; poly(N-(2-hydroxypropyl) methacrylamide), poly(I-aspartamide), DLPLA-poly(dl-lactide), poly (L-Lactic acid); LPLA-poly (I-lactide), PDO-poly (dioxanone), PGA-TMC-poly (polyglycolide-co-trimethylene carbonate), PGA-LPLA-poly(I-lactide-co-glycolide), PGA-DLPLA-poly(dl-lactide-co-glycolide), LPLA-DLPLA-poly(I-lactide-co-dl-lactide), PDO-PGA-TMC-poly(glycolide-co-trimethylene carbonate-co-dioxanone), or any combination thereof.

In some applications, it may be desirable to induce an inflammatory response in the vicinity of the tissue proximal to the deployed device so as to promote the formation of scar tissue. For example, in flow diversion applications directed at treating an aneurysm, the promotion of scar tissue in the blood vessel wall at the neck of the aneurysm as it heals may improve the strength of the vessel at the site and reduce the risk that an aneurysm will redevelop. For such applications, embodiments employing a bioabsorbable polymeric fiber that forms lactic acid upon degradation may be useful. Accumulating acidic degradation products decrease the pH of the surrounding tissue, which may trigger inflammatory and foreign body reactions at the site of the pathology. Implantation of PLLA scaffolds in the coronary arteries of mini-pigs results in expression of NF-kB a marker of inflammation that mediates expression of numerous inflammatory cytokines. Accordingly, particular embodiments of the invention may utilize bioabsorbable polymeric fibers that comprise polylactides (PLA), polylactide-co-glycolides (PLGA), DLPLA-poly(dl-lactide), poly (L-Lactic acid); LPLA-poly(I-lactide), PGA-LPLA-poly(I-lactide-co-glycolide), PGA-DLPLA-poly(dl-lactide-co-glycolide), LPLA-DLPLA-poly(I-lactide-co-dl-lactide), or any combination thereof.

The devices disclosed herein display special structural features when axially extended/expanded or compressed. When expanded, the structure is capable of substantially accommodating strain or stress forces since the initially inclined fibers are free to pivot to a position parallel to the direction of the stress. In addition, individual polymeric fibers may slide up against each other providing elastic and flexible properties to the device.

Visualization Aids

This braided assembly exhibits special structural features when axially extended or compressed. When extended, the structure is capable of substantially accommodating strain or stress forces since the initially inclined fibers are free to pivot to a position parallel to the direction of the stress. In addition, individual polymeric fibers may slide up against each other providing elastic and flexible properties to the device.

It is critical for the physician deploying a device within a body lumen to be able to determine the position of the device within the lumen. Thus, it is desirable for devices as disclosed herein to include a visualization aid. Accordingly, various embodiments of the implantable devices disclosed herein will comprise a radio-opaque material to facilitate imaging of the device in the body lumen by X-ray fluoroscopy.

Such radio-opaque materials may include tantalum, platinum; tungsten, gold; iodine; or combinations thereof. The radio-opaque material may be selected according to the polymeric material of the bioabsorbable polymeric fiber, the imaging technology; the pathology to be treated; etc.

A radio-opaque material may be attached or in contact with polymeric fibers in various ways, for example by covalent bonding of a radio-opaque material with a bioabsorbable polymeric fiber; adhesion of a radio-opaque material to a bioabsorbable polymeric fiber; or other forms of attachment, contact; bonding; blending or incorporation of the radio-opaque material with the polymeric fibers.

Figure 6A:
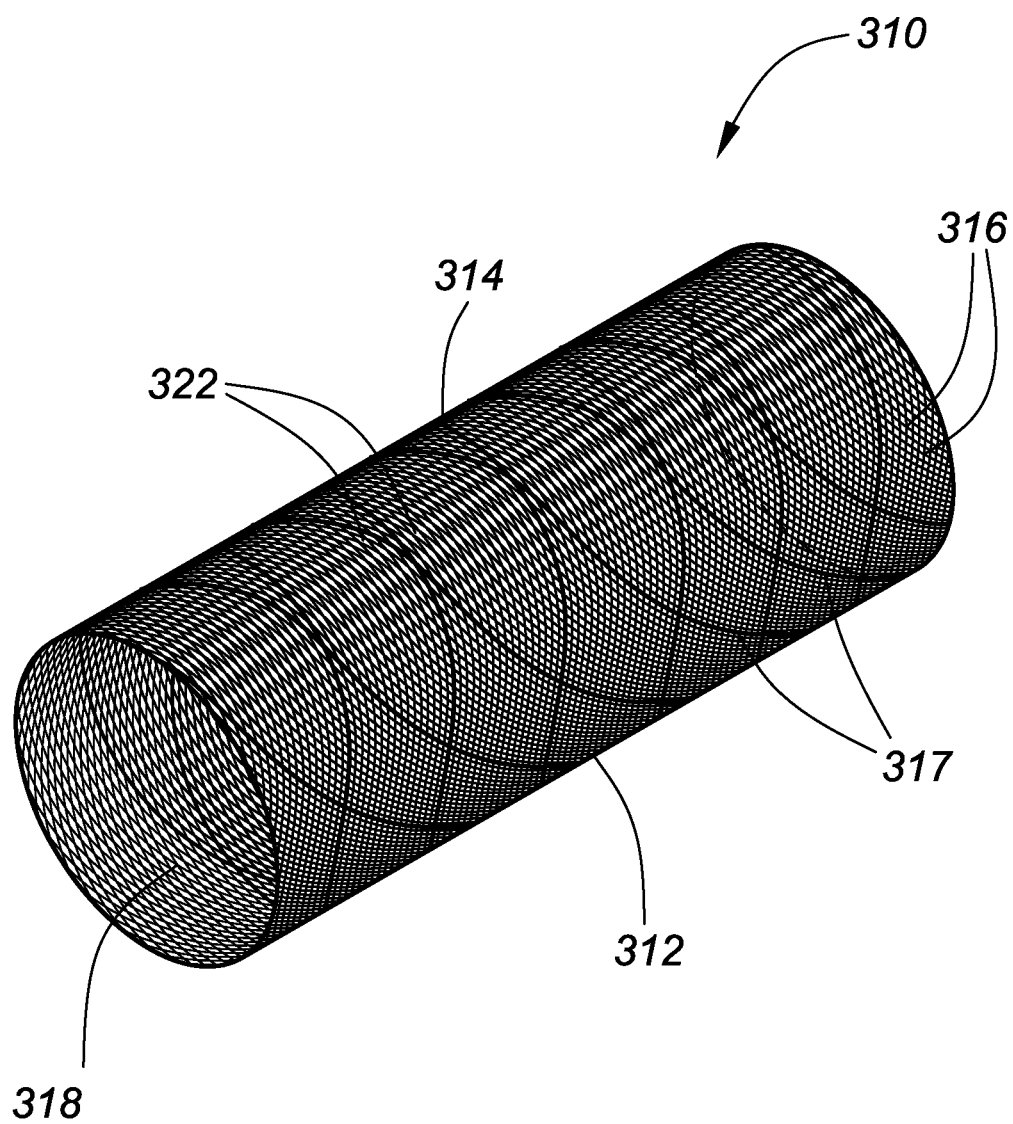
FIG. 6A is an isometric view of an implantable device according to a second embodiment of the invention comprising a braid of interwoven bioabsorbable polymeric fibers and radio-opaque material.
Figure 6B:
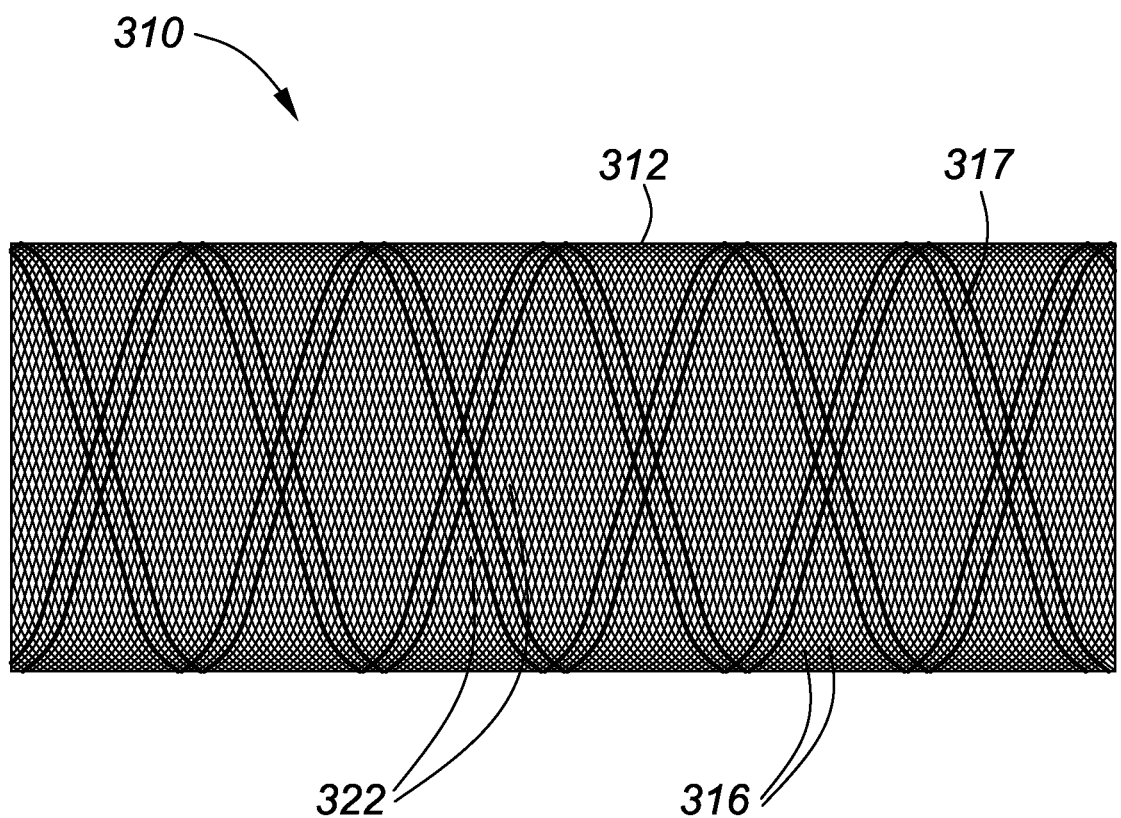
FIG. 6B is a side view of the device illustrated in FIG. 6A.

Referring to FIGS. 6A; 6B, 7A, 7B; 8A; and 8B; a device for positioning with a body lumen to achieve flow diversion of a bodily fluid according to a second embodiment of the invention comprising a visualization aid is shown generally at 310. Device 310 comprises a resiliently deformable tubular body 312 formed of a braid 314 of interwoven bioabsorbable polymeric fibers 316. Referring to FIG. 1; tubular body 312 defines a lumen 318 through which a bodily fluid can continue to flow when device 310 is deployed within a body lumen. A visualization aid is provided by four radio-opaque wires 317 that are interwoven with bioabsorbable polymeric fibers 316 to form part of braid 314. Overlapping bioabsorbable polymeric fibers 316 and radio-opaque wires 317 define pores 322.

Figure 7A:
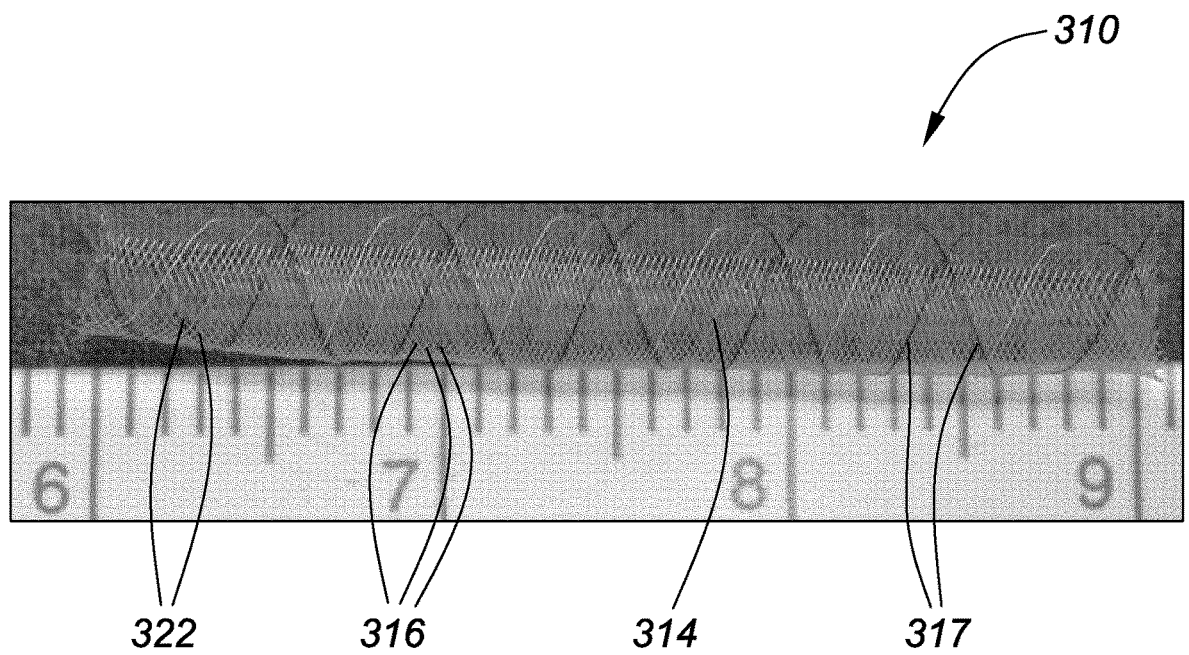
FIG. 7A is a picture of an embodiment of an implantable endovascular device comprising 44 interwoven poly L-lactic acid (PLLA) polymeric fibers and 4 radio-opaque wires.
Figure 7B:
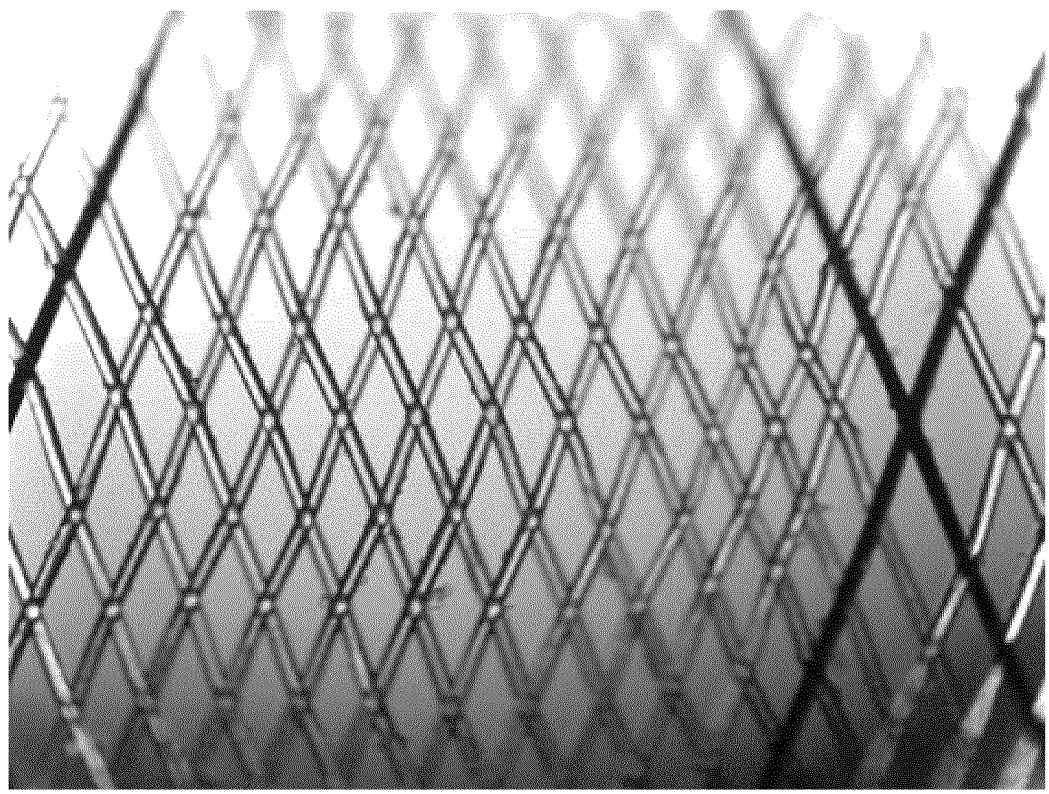
FIG. 7B is a close up picture of the device of FIG. 7A.

The embodiment depicted in FIG. 7 utilizes 44 bioabsorbable polymeric fibers and 4 radio-opaque wires. The embodiment depicted in FIG. 8A utilizes 46 bioabsorbable polymeric fibers and 2 radio-opaque wires. However, any number of radio-opaque wires could be used as a visualization aid. The number used may depend on a variety of factors including the nature of the radio-opaque material. As few as a single radio-opaque wire may be sufficient. However; the ability to visualize the device improves with the number of radio-opaque wire utilized. In various embodiments, 2; 3, 4, 5, 6, 7, 8; 9; 10, or 12 radio-opaque wires may be utilized. Preferably, an even number of radio-opaque wires is utilized to maintain balance. In preferred embodiments; 6 radio-opaque wires or 8 radio-opaque wires are utilized. The skilled person will understand that resolution of the device may decrease with increasing number of radio-opaque wires and thus the selected number will reflect a balance between detectability and sharpness of the image.

As indicated above, the radio-opaque wires 317 may comprise radio-opaque materials such as tantalum, platinum, tungsten, gold, iodine; or combinations thereof. In particular embodiments; the radio-opaque wires may be resiliently deformable. In some embodiments; the resiliently deformable wires are made from a nickel-titanium alloy (e.g. nitinol), a cobalt-chromium alloy (e.g. Phynox); or a cobalt-chromium-nickel alloy. Each resiliently deformable wire may independently be made of a nickel-titanium alloy coated with the radio-opaque material; a drawn filled tube (DFT) comprising a nickel-titanium alloy exterior and a core comprising the radio-opaque material, a DFT comprising an exterior comprising the radio-opaque material and a core comprising a nickel-titanium alloy, a cobalt-chromium-nickel alloy coated with the radio-opaque material; a DFT comprising a cobalt-chromium-nickel alloy exterior and a core comprising the radio-opaque material; or a DFT comprising an exterior comprising the radio-opaque material and a core comprising cobalt-chromium-nickel alloy. In particular embodiments; the radio-opaque wire is a tantalum-coated nitinol wire. In other embodiments; the radio-opaque wire comprises a DFT having a nitinol exterior and a platinum core.

Facilitating and Maintaining Expansion

It is important that, upon deployment in a lumen; the exterior surface of the tubular bodies of the presently disclosed devices remains closely appressed to the body wall; particularly in devices for flow diversion applications in blood vessels. If the exterior surface of the tubular body is not closely appressed to the blood vessel wall, thromboses will form in the spaces between the tubular body and the blood vessel wall, and lead to occlusion of the blood vessel. While embodiments of the devices disclosed herein that include only bioabsorbable polymeric fibers are resiliently deformable, they may be at prone to shrinkage or partial collapse within the blood vessel. Moreover; the bioabsorbable polymeric fibers may have a tendency to lose some of their ability to self-expand when stored in a compressed state for a prolonged period of time.

Accordingly, various embodiments of the devices disclosed herein include means for facilitating and/or maintaining radial expansion of the tubular body in the body lumen so as to maintain the exterior surface of the tubular body closely appressed to the body wall. Such means also assist in facilitating and/or maintaining axial expansion of the device. Accordingly facilitating and/or maintaining radial and/or axial expansion may contribute to self-expansion of the device upon deployment in the lumen.

The means for facilitating and/or maintaining radial and/or axial expansion of the tubular body in the body lumen may include a wire interwoven with the plurality of bioabsorbable polymeric fibers to form part of the braid. In operation, the wire exerts a radial force on the tubular structure to facilitate radial expansion upon deployment and to urge the tubular structure against the body wall to maintain the tubular structure in fully expanded form and appressed to the body wall. In particular embodiments, the wire is resiliently deformable. The resiliently deformable wire may comprise a nickel-titanium alloy or a cobalt-chromium-nickel alloy.

As few as a single wire may be sufficient to facilitate and maintain radial and/or axial expansion of the tubular body. However, the radial force exerted by the tubular body as it expands will increase with the number of wires used. In various embodiments, 2, 3, 4, 5, 6, 7, 8, 9, 10, or 12 radio-opaque wires may be utilized. Preferably, an even number of radio-opaque wires is utilized to maintain balance. In preferred embodiments, 6 radio-opaque wires or 8 radio-opaque wires are utilized.

It will be readily apparent to the skilled person that the same wires may be used as both a visual aid and as a means for facilitating and/or maintaining radial and/or axial expansion. Accordingly, the wires may comprise radio-opaque materials such as tantalum, platinum, tungsten, gold, iodine, or combinations thereof. In particular embodiments, the radio-opaque wires may be resiliently deformable. In some embodiments, the resiliently deformable wires are made from a nickel-titanium alloy (e.g. nitinol), a cobalt-chromium alloy (e.g. Phynox), or a cobalt-chromium-nickel alloy. Each resiliently deformable wire may independently be made of a nickel-titanium alloy coated with the radio-opaque material, a drawn filled tube (DFT) comprising a nickel-titanium alloy exterior and a core comprising the radio-opaque material, a DFT comprising an exterior comprising the radio-opaque material and a core comprising a nickel-titanium alloy, a cobalt-chromium-nickel alloy coated with the radio-opaque material, a DFT comprising a cobalt-chromium-nickel alloy exterior and a core comprising the radio-opaque material, or a DFT comprising an exterior comprising the radio-opaque material and a core comprising cobalt-chromium-nickel alloy. In particular embodiments, the radio-opaque wire is a tantalum-coated nitinol wire. In other embodiments, the radio-opaque wire comprises a DFT having a nitinol exterior and a platinum core.

Accordingly, a metal wire component may provide at least three independent advantage, namely: 1) allowing for radio-opacity and thus visualization by means of X-ray fluoroscopy; 2) improving self-expandability, and 3) improving radial force to maintain radial expansion (crush force and chronic outward force) to maintain the outer wall of the tubular body closely appressed to the body wall.

Manufacture

Referring back to FIGS. 4 and 5, a device as disclosed herein may be formed, for example, from individual interwoven bioabsorbable polymeric fibers and, in various embodiments, radio-opaque wires to create a braid forming the tubular body.

Braiding the tubular bodies on, for example, a "maypole style" machine avoids the need for known laser cutting techniques for manufacturing a device for deployment in a body lumen. Instead, bioabsorbable polymeric fibers of varying diameters may be braided on a mandrel at varying pitch angles to produce braided, hollow, and tubular bodies with varying porosities. The braid may be a linear fibrous assembly with sets of interlacing bioabsorbable fibers that lie on a bias relative to the longitudinal axis of the structure. The braiding may be clockwise or counterclockwise interlacing or spiraling fibers.

Several patterns of braids or interlacing fibers may be used. The present invention is not limited to any of the following examples: a "1-over-1-under-1" or "half load" pattern; a "2-under-2-over-2" or "diamond" pattern; a "1-under-2-over-2" (otherwise known as "1-over-2-under-2") or "full load" pattern; or other variations.

For the 1-under-2-over-2 pattern, a 48 carrier machine can be used to produce a 48 fiber design. For a 1-over-1-under-1 pattern, a 96 carrier machine is required for the design that also still comprises 48 fibers. The desired pattern may depend on several factors including tubular body width; bioabsorbable polymeric fiber diameter, and the particular bioabsorbable polymeric. For example, 2-under-2-over-2 increases braid thickness and thus influences the choice of possible tubular bodies that can be made with this pattern.

Referring to FIG. 5, and as described above, the pitch angle of the braid is the angle formed by between bioabsorbable polymeric fibers 280 (or wires 290), as they extend from carriers 250 to mandrel 270, and the transverse axis 275 of the mandrel 270 (i.e. the perpendicular axis to the longitudinal direction of mandrel 270).

Referring still to FIG. 5; in embodiments that involve optionally radio-opaque wires; wires 290 are preferably loaded as pairs on opposing carriers 240 to that forces are balanced within the braided product.

With respect to embodiments disclosed herein that involve resiliently deformable radio-opaque wires that require heat treatment to set the original shape of the wire; it may not be necessary or desired to set the shape of the wire in some embodiments. However, where it is desired to set the original shape of the wire, it is important to note that they should not be shape set (or "annealed") straight; as this would adversely affect the lower radial exerted by the tubular body upon expansion, and result in an inability to cause the tubular body to adequately expand after being deformed or delivered through a catheter. Thus, it is preferable to shape set the wire on the mandrel. However, it is undesirable to shape set the wire on the mandrel with the bioabsorbable polymeric fibers because; in order to shape set the wire, it is necessary to heat the wire to a temperature of upwards of 500 degrees Celsius, which would melt the bioabsorbable polymer fibers if they were on the mandrel at the same time as the wires. One option may be to shape set the wired on a mandrel without the polymer fibers. The shape set wire could then be rewound into the bobbin and then braided with the bioabsorbable polymeric fibers. Another option may be to shape set the final braided design at a lower temperature (e.g.) in order to relieve any residual stress on the polymer fibers. This would essentially shape set the bioabsorbable polymer fibers; but not the radio-opaque wires, in the final design. As described above; another option is to simply forgo shape setting the wire or bioabsorbable polymeric fibers.

Some metal wires may flare out at the ends of the scaffold upon production; which could result in puncture of the body wall (e.g. a blood vessel) upon delivery. The flaring of the metal wires could also depend on where the scaffold is cut from the mandrel. For example; if the scaffold is cut precisely at the point where two metal wires overlap; there will likely be less flare-out. Accordingly; it may be preferable in some embodiments to solder the metal wires together.

Therapeutic Agent Delivery

The devices disclosure herein may also be useful for delivering a therapeutic agent to a pathology of or proximal to a body wall defining the lumen. The bioabsorbable polymeric fibers of the tubular body may be coated with or conjugated to the therapeutic agent, or the therapeutic agent may be incorporated within the bioabsorbable polymeric fiber. The therapeutic agent may be slowly released over time to treat the pathology. In the context of an endovascular device for implantation in a blood vessel, the therapeutic agent may be an antibiotic agent, an antiviral agent, an analgesic, a muscle relaxant, a chemotherapeutic agent, an intra-arterial vasodilating agent, a calcium channel inhibitor, a calcium channel antagonist, a calcium channel blocker, a transient receptor potential protein blocker, an endothelin antagonist; a blood thinning agent, an antiplatelet agent, or any combination thereof.

In various embodiments, the therapeutic agent may include paclitaxel; sirolimus; everolimus, temozolamide, cyclophosphamide, doxorubicin, irinotecan, azathioprine, methotrexate, cisplatin; or vincristine. In the particular context of a flow diverting device as disclosed herein for treatment of an aneurysm, the therapeutic agent may include one or more blood thinners/antiplatelet agents such as aspirin, heparin, Ticagrelor; 5-fluorouracil, melphalan; or clopidogrel.

The therapeutic agents may also be used in the form of their pharmaceutically acceptable salts or derivatives and in the case of chiral active ingredients. It is also possible to employ both optically active isomers and racemates or mixtures of diastereoisomers. As well; a therapeutic agent may include a prodrug; a hydrate; an ester; a derivative or analogs of a compound or molecule.

As discussed above, the polymeric material itself may, in some contexts, provide lactic acid upon degradation, which may aid in healing and strengthening body wall at the site of the pathology such as an aneurysm.

The therapeutic agents may elute over a controlled period of time, which is shown to be effective; to minimize side effects. A device as disclosed herein may be placed at a site proximal to the pathology. In this way, the therapeutic agent can be targeted to the disease while side effects may be minimized; as the therapeutic agent may not be distributed to organs that do not involve the disease; as in the case of oral administration or intravenous administration of therapeutic agent.

At least two mechanisms may regulate the release kinetics of a therapeutic agent: 1) a diffusion-controlled mechanism, in which the therapeutic agent diffuses outwardly through the bulk polymer due to a concentration gradient, and 2) a degradation-controlled mechanism, in which release of the therapeutic agent depends on the hydrolytic or other degradation of the polymeric material and erosion of polymeric fiber surface.

A device of the present disclosure may be configured so that the initial release of the therapeutic agent can be deferred to correspond to the delayed clinical manifestations of the disease. The desired timing of therapeutic agent release may vary, for example, it may be immediate for patients who already have a disease. A device may alternatively be used prophylactically in patients who are at high risk of developing a disease or pathology; in which case the desired timing of drug release may be delayed.

A device of the present disclosure may also be configured so that the release of the therapeutic agent is triggered by the introduction of another therapeutic agent, a physiological condition; or any change within the bodily lumen.

Operation

The presently disclosed devices comprising resiliently deformable tubular bodies may self-expand when deployed within a bodily lumen. The degree of expansion may depend on the polymeric material, crystallinity of the polymer, diameter of the polymeric fiber; diameter of the tubular body; pitch angle of the weave, physiological conditions; polymer annealing temperature or the structural contribution of any included material such as a radio-opaque material or similar parts. Various embodiments of the devices disclosed herein may exhibit memory self-expansion in the body.

The resiliently deformable and self-expanding features of the tubular bodies of the devices disclosed herein allow them to be configured in a radially compressed state for intraluminal catheter implantation. Once properly positioned adjacent the pathology in the body lumen, the device is allowed to expand radially and axially such that the outer surface of the tubular body becomes appressed to the body wall defining the lumen. Radial expansion of the device may be assisted by inflation of a balloon attached to the catheter.

The devices disclosed herein may be pre-loaded in a kit, for example in a sheath or a micro-catheter for ease of delivery or for immediate deployment. The kit may include a device as disclosed herein pre-loaded within a delivery system suitable for inserting the device into a patient, delivering the device through the lumen of a body; e.g. the vascular system of a patient; and deploying the device to the desired position for implantation of the device within the body of the patient. The delivery system may include a sheath; a catheter, a guide wire, and/or any other elements for insertion, delivery, guiding, deployment, and implantation of the vascular device, or combinations thereof.

Figure 9A:
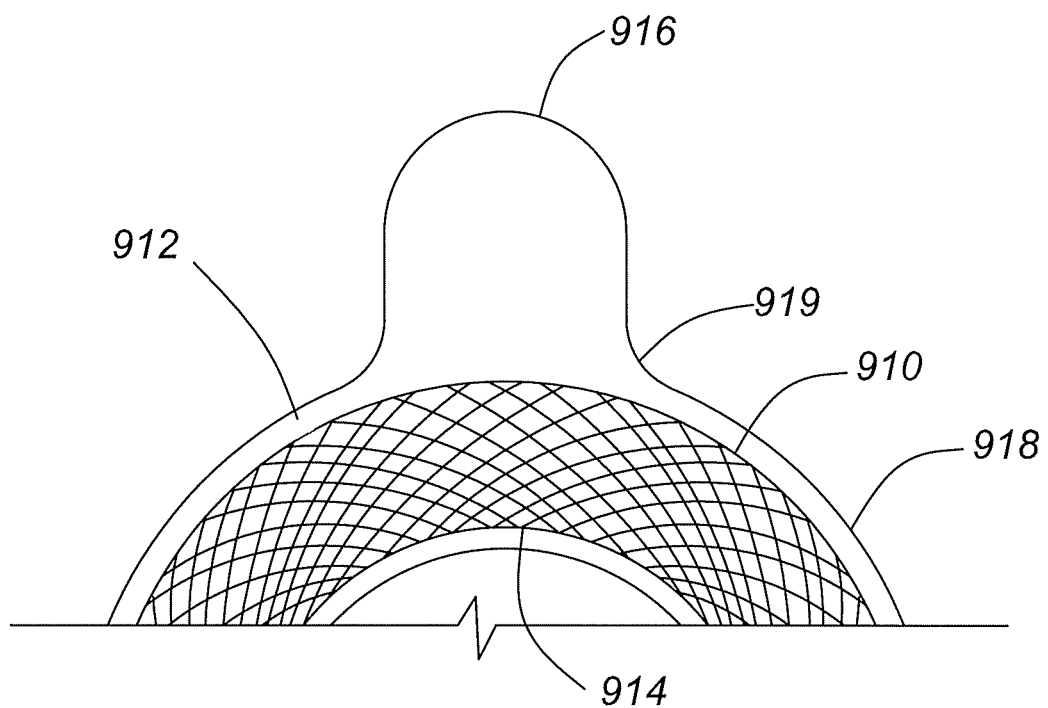
FIG. 9A is a schematic diagram of a flow diverting application to treat of an aneurysm.
Figure 9B:
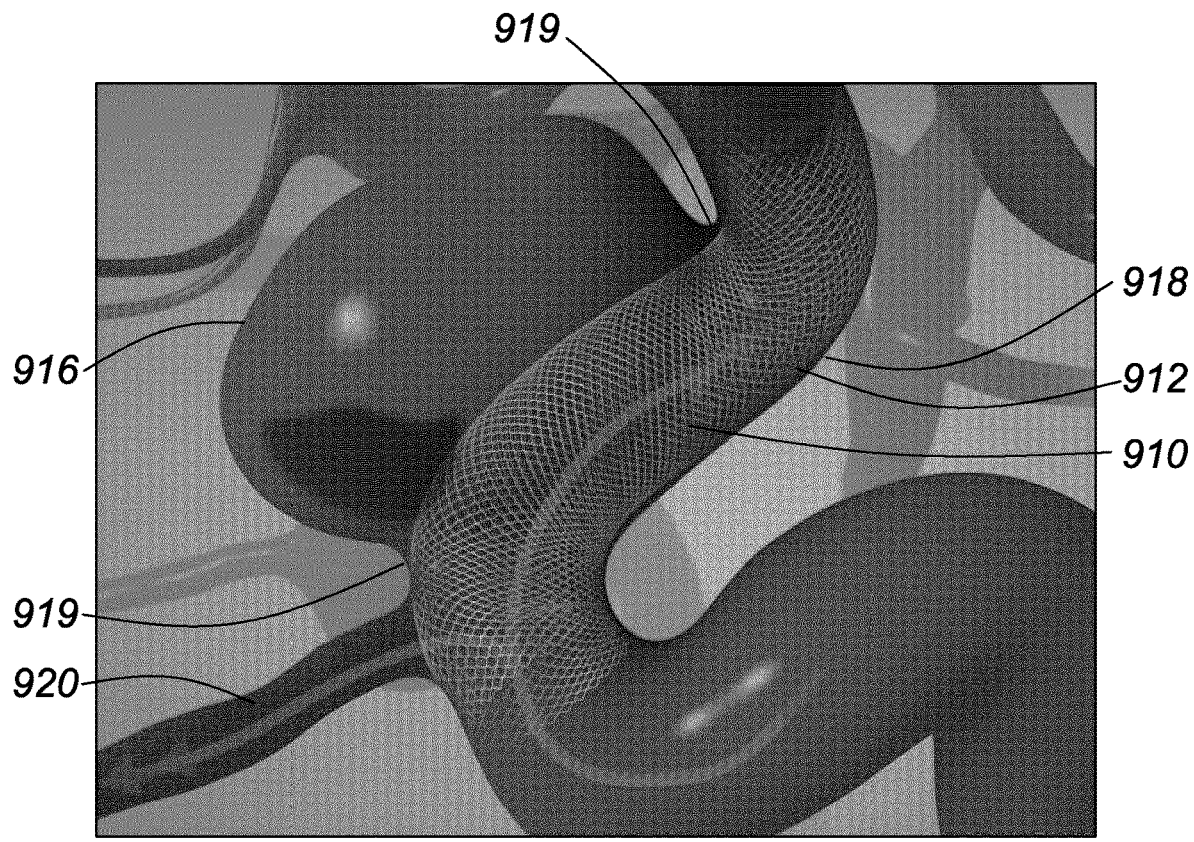
FIG. 9B is a schematic diagram of a flow diverting application to treat of an aneurysm.

According to one embodiment of the disclosure, an endovascular device of may be configured to divert blood flow away from the downstream intravascular territory or the site of a disease. In particular, diversion of blood through the vascular network may be necessary to prevent or treat an unruptured or ruptured brain aneurysm. Referring to FIGS. 9A and 9B; endovascular device 910 is thus deployed in the lumen 912 defined by blood vessel wall 918 proximal to the aneurysm 916 and allowed to expand such that, when tubular body 914 is full expanded; the outer surface of the tubular body is closely appressed to the blood vessel wall 918 and spans the neck 919 of the aneurysm. The low porosity of the braid thus diverts flow of blood past the neck of the aneurysm 916. At the same time, the braid is sufficiently porous to permit a small amount of blood to enter the aneurysm sac with low velocity, which causes thrombosis and occlusion of the aneurysm, and permits the aneurysm to heal. Referring to FIG. 9B, the braid is also sufficiently porous to permit enough blood to flow throw through the pores to healthy blood vessel branches, e.g. branch 920; that may also be spanned, or partially spanned, by the device, thereby maintaining their patency.

Figure 10:
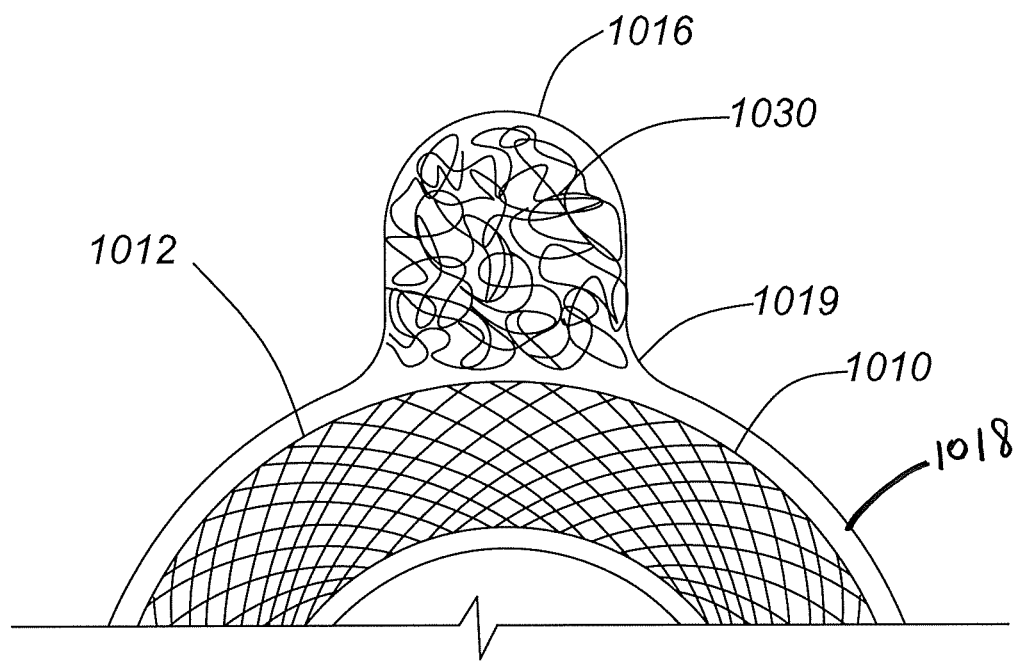
FIG. 10 is a schematic diagram of a flow diverting application in combination with an aneurysm-bridging application.

In another embodiment; an endovascular device according to an embodiment disclosed herein may be used to support coils placed into the aneurysm to prevent prolapse into a parent blood vessel; for example by aneurysm-bridging. The endovascular device may be configured to fit into a bodily lumen in combination with metal coils or a balloon. Referring to FIG. 10, the aneurysm neck 1019 may be wide. In such circumstances the endovascular device 1010 can serve to remodel the neck 1019 and support the metal coils 1030 placed into the aneurysm 1016. The endovascular device can prevent the metal coils from travelling within the body lumen 1012 defined by blood vessel wall 1018, for example preventing the coils from entering a parent blood vessel. After the procedure; the endovascular device 1010 will typically be left in place, but may be removed in some embodiments. In another embodiment; the endovascular device may be configured to fit into a bodily lumen to support the metal coils in any manner.

EXAMPLES

While specific embodiments of the invention have been described and illustrated; such embodiments should be considered illustrative of the invention only and not as limiting the invention as construed in accordance with the accompanying claims.

Example 1

Referring to FIG. 4, a device was made constructed with 48 bioabsorbable polymeric fibers of poly-L-lactic acid with a molecular weight of 30.000 g/mol and a diameter of 50 µm.

Example 2

Referring to FIG. 7, a device was made constructed with 44 bioabsorbable polymeric fibers of poly-L-lactic acid with a molecular weight of 30;000 g/mol and a diameter of 50 µm interwoven with four radio-opaque fibers of tantalum-coated nitinol. The device was tested in animal blood vessels, i.e. rabbit aortas; and was able to keep important vascular side branches open without occluding any of the blood vessels.

Figure 11A:
FIG. 11A is an early arterial phase angiogram taken before device implantation; showing an aneurysm created in a rabbit carotid artery with a daughter sac at the tip of the aneurysm.
Figure 11B:
FIG. 11B is an early venous phase angiogram of the same aneurysm shown in FIG. 19A (same angiographic run as above) before device implantation, demonstrating rapid contrast washout except in the daughter sac.
Figure 11C:
FIG. 11C is an early venous phase angiogram of the same aneurysm shown in FIGS. 19A and 19B after placement of the device, demonstrating contrast stagnation in the body of the aneurysm indicative of a flow diverting effect.

FIGS. 11A and 11B are time lapse photos of an angiogram of an aneurysm during early arterial and early venous phase prior to implantation of the device. The rapid washout of signal from the aneurysm shown in FIG. 11B is indicative of fluid flow into the aneurysm. In contrast; FIG. 11C shows early venous phase after implantation of the device; wherein signal is retained in the aneurysm. This indicates that blood is no longer flowing freely into the aneurysm and that the device is successfully diverting flow from the aneurysm.

Figure 12A:
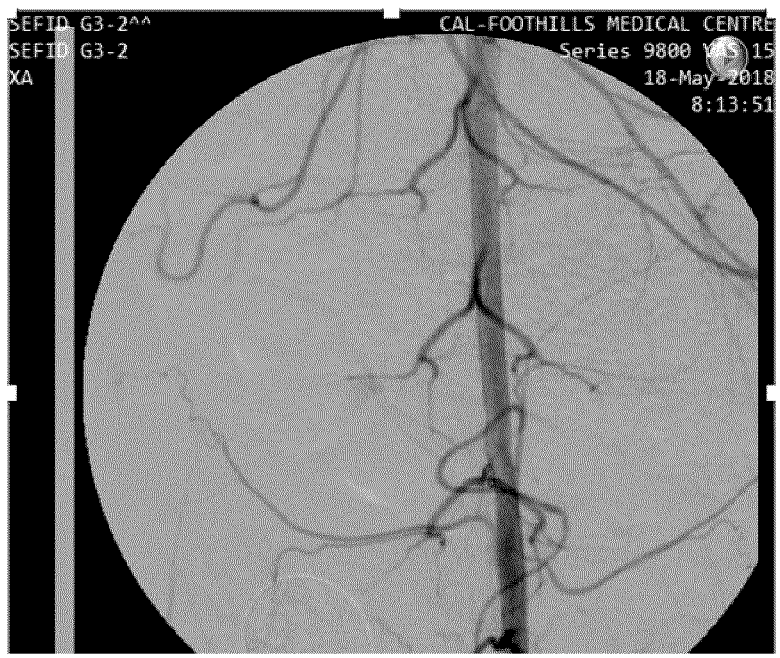
FIG. 12A is an angiogram of a rabbit aorta immediately after implantation of a device comprising 44 bioabsorbable PLA fibers and radio-opaque Tantalum-coated nitinol fibers.
Figure 12B:
FIG. 12B is an angiogram of the rabbit aorta depicted in FIG. 14A 1 month after implantation of the device.
Figure 13:
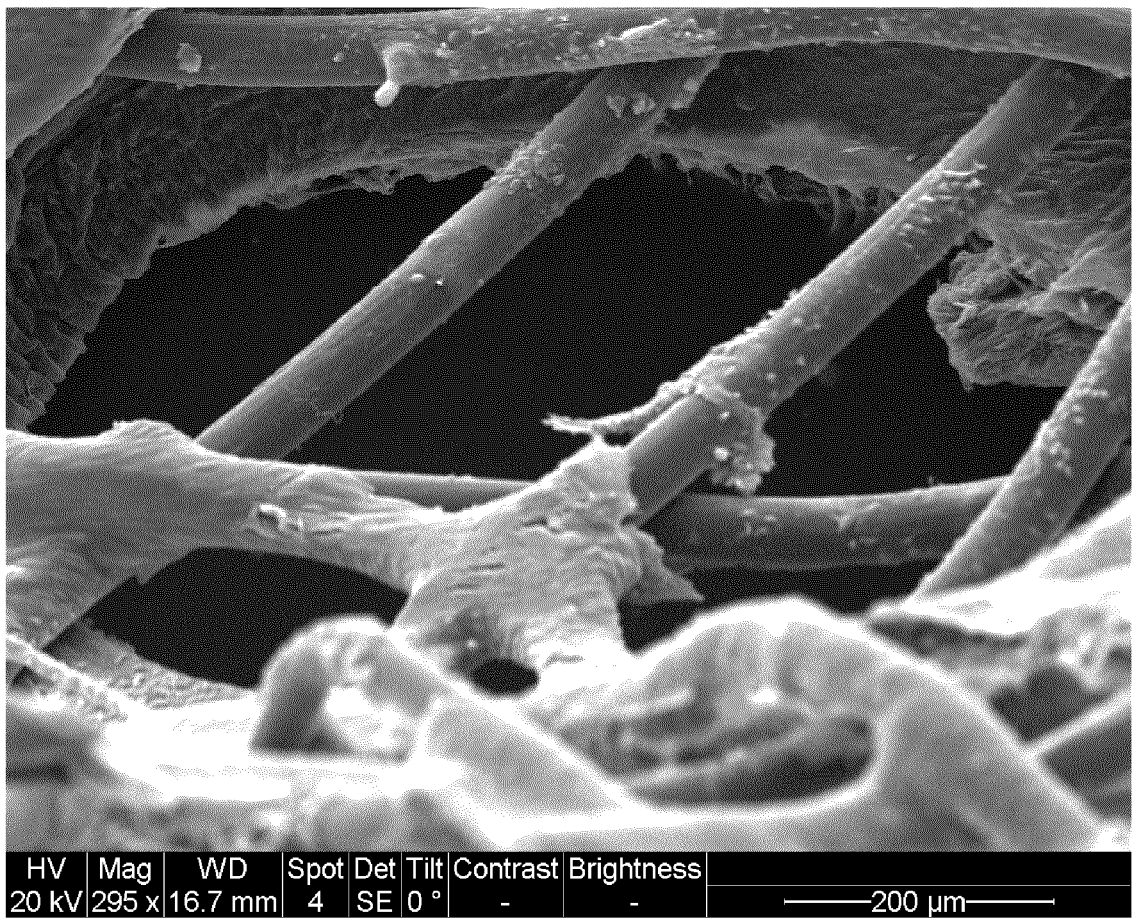
FIG. 13 is a scanning electron micrograph (SEM) showing persistent patency of a side branch of a rabbit aorta 1 month after implantation of the device.

Referring to FIGS. 12A and 12B, rabbit aortas into which the device was deployed showed persistent angiographic patency of the aorta where the device was placed as well as the "jailed" side branches after 1 month (FIG. 12B). FIG. 13 is a scanning electron micrograph of showing persistent patency of a side branch of the rabbit aorta after 1 month implantation of the device.

Figure 14:
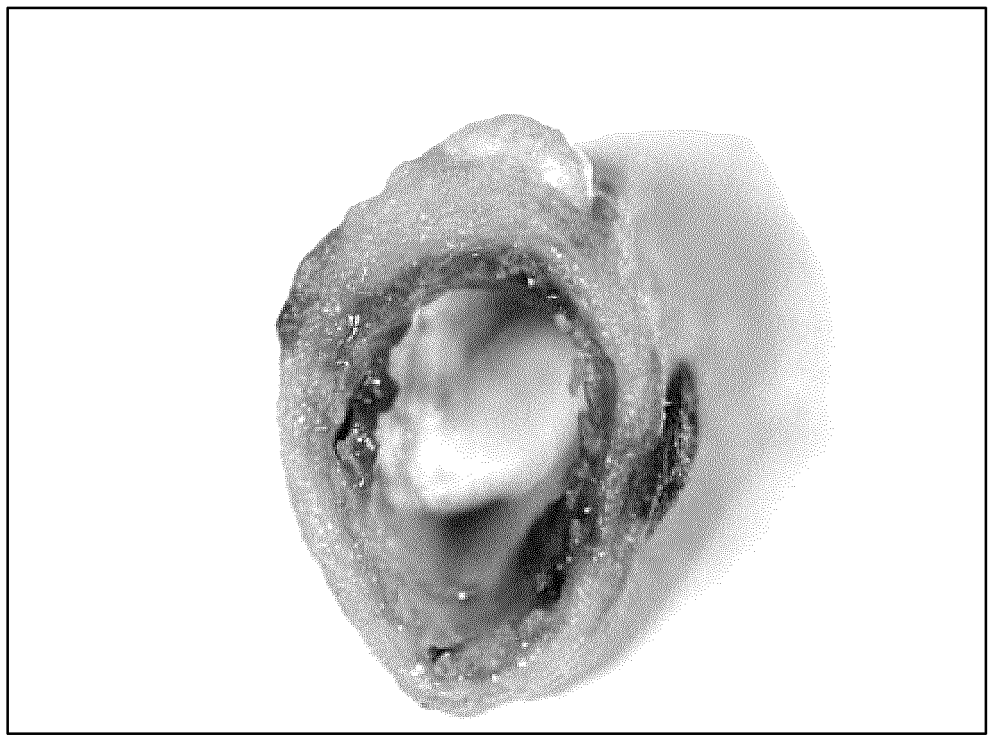
FIG. 14 is a gross histology picture of a device comprising 44 bioabsorbable PLA fibers and 4 radio-opaque Tantalum-coated nitinol fibers after implantation in a rabbit aorta.

Referring to FIG. 14; the device showed excellent blood vessel wall apposition.

Figure 15:
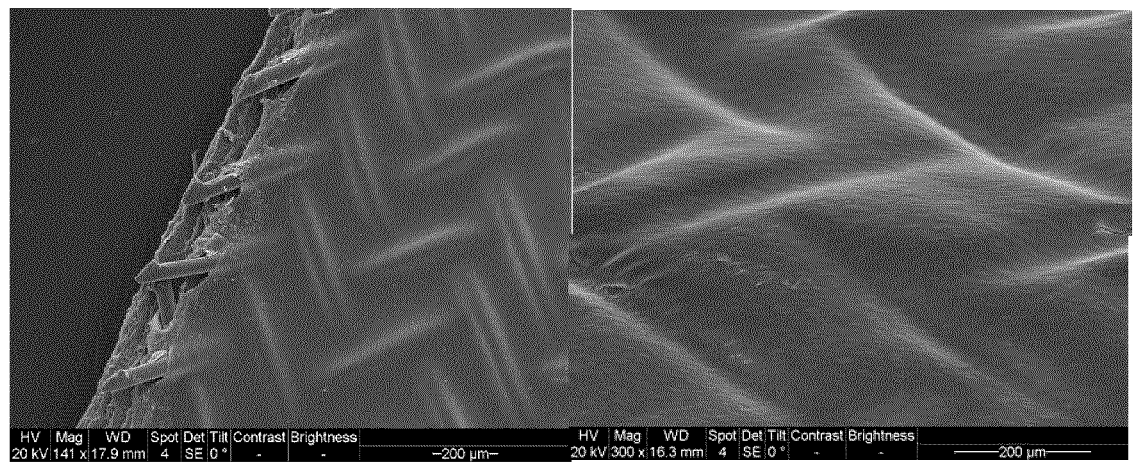
FIG. 15 are scanning electron micrographs (SEM) showing a smooth neointimal layer forming over the stent struts 1 month after implantation of the device into the rabbit aorta.

FIG. 15 is scanning electron micrographs of showing a smooth neointimal layer forming over interior surface of the tubular body 1 month after implantation of the device.

Figure 16A:
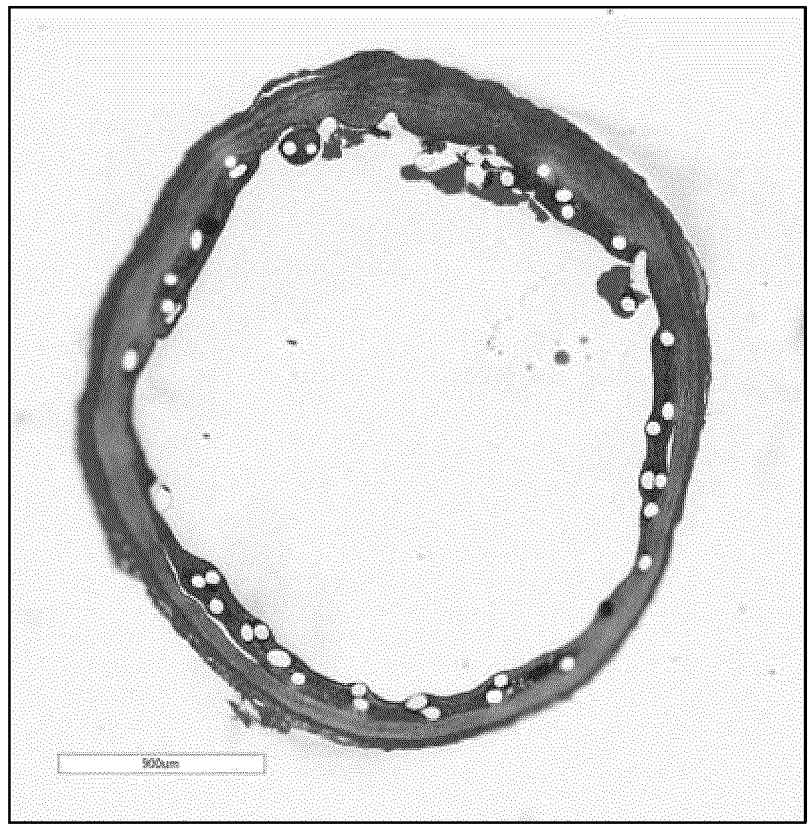
FIG. 16A is a histological cross section of a rabbit aorta showing persistence of polymer fibers and neointima formation over the fibers one month after implantation of a device.

FIG. 16A is a histological cross section of a rabbit aorta showing persistence of polymer fibers and neointima formation over the fibers one month after implantation of a device.

Figure 16B:
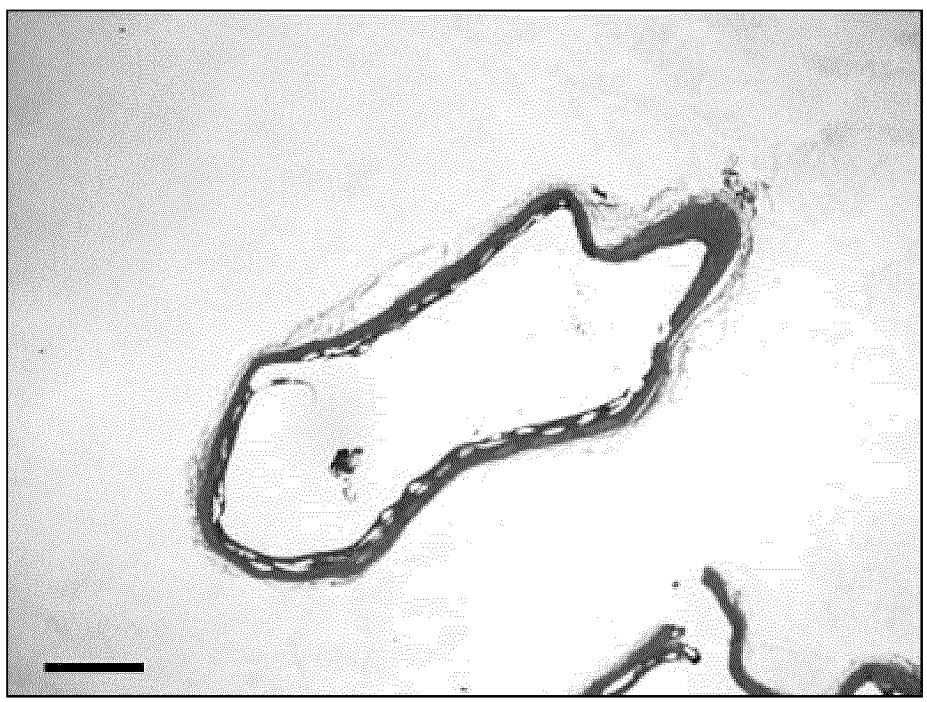
FIG. 16B is a histological cross section of a rabbit aorta showing persistence of polymer fibers, neointima formation over the fibers, and a lack of exuberant inflammatory response two months after implantation of a device.
Figure 17:
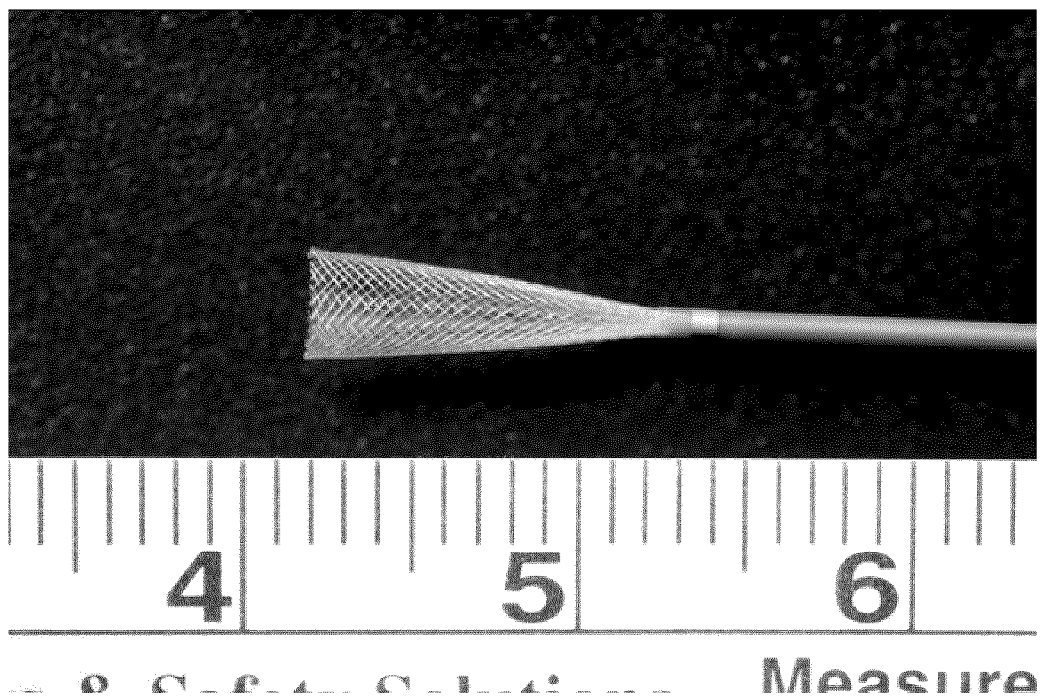
FIG. 17 is a picture of a device according to an embodiment disclosed herein consisting only of bioabsorbable PLLA polymeric fibers, illustrating its ability to self-expand after being loaded into; then pushed out of, a catheter with an inner diameter of 0.027".

FIG. 16B is a histological cross section of a rabbit aorta showing persistence of polymer fibers; neointima formation over the fibers, and a lack of exuberant inflammatory response two months after implantation of a device.

The lack of an exuberant inflammatory response on histology at 2 months is believed to be due to the thin diameter of the bioabsorbable polymeric fibers (roughly 50 microns). The presently disclosed scaffolds contrast with the thick struts of the previously FDA approved laser-cut bioabsorbable stent (marketed and sold by Abbott Vascular as the Absorb BVS stent).

The formation of the neointima over the interior surface of the interior body; the lack of an exuberant inflammatory response as indicated by histology at 2 months, demonstrates the biocompatibility of the device with the blood vessel wall. Response of the blood to the polymer material is important because it can result in unwanted thrombosis or hemolysis. The thromobgenicity of the device was compared to that of the leading metal flow diverting device (i.e. Pipeline™) in terms of thrombotic response. The device of the present disclosure showed a lower % thrombosis surface coverage as well as a lower hemolytic index compared to i.e. Pipeline™ as indicated in Table 2 and Table 3.

Table 2 shows a lower % thrombosis surface coverage for the device of the present disclosure compared with Pipeline™ (tests done as per ISO standards).

TABLE 2

| Sample type (N = 3 for each) | % lumen occlusion | % thrombosis surface coverage |
| --- | --- | --- |
| Positive control | 100% | 100% |
| Negative control | 0% | 0% |
| Comparative sample (Pipeline ™) | 0% | 3.6% |
| Bioabsorbable Stent | 0% | 2.3% |

Table 3 provides the results of in vitro hemolysis studies (performed according to AS™ standards), showing a lower hemolytic index of the presently disclosed device compared with Pipeline™.

TABLE 3

| Experiment Type | Replicate | Plasma hemoglobin (mg/ml) | Total hemoglobin (mg/ml) | Hemolytic Index | Mean Hemolytic Index |
| --- | --- | --- | --- | --- | --- |
| Pipeline (Predicate) Control | 1 | 1.11 | 185.74 | 0.5 | 0.5 |
| | 2 | 0.88 | 211.56 | 0.8 | |
| | 3 | 1.21 | 196.35 | 0.6 | |
| Negative Control (glass) | 1 | 1.11 | 185.74 | 0.03 | 0.02 |
| | 2 | 0.88 | 211.56 | 0.01 | |
| | 3 | 1.21 | 196.35 | 0.02 | |
| Positive Control | 1 | 1.11 | 185.74 | 12.9 | 15.5 |
| | 2 | 0.88 | 211.56 | 15.6 | |
| | 3 | 1.21 | 196.35 | 17.9 | |
| Bioabsorbable Stent | 1 | 1.11 | 185.74 | 0.4 | 0.4 |
| | 2 | 0.88 | 211.56 | 0.6 | |
| | 3 | 1.21 | 196.35 | 0.2 | |

Without wishing to be bound by theory, it is believed that the small diameter of the bioabsorbable polymeric fibers (about 50 μm) contributes to this observed biocompatibility. In comparison; the comparatively thick polymeric fibers of previously FDA approved, laser-cut bioabsorbable devices having fibers of about 150 μm in diameter (marketed and sold by Abbott Vascular as the Absorb BVS) were prone to causing thrombosis (see Expert Opin Drug Deliv. 2016 October; 13(10):1489-99).

Example 3

Figure 8A:
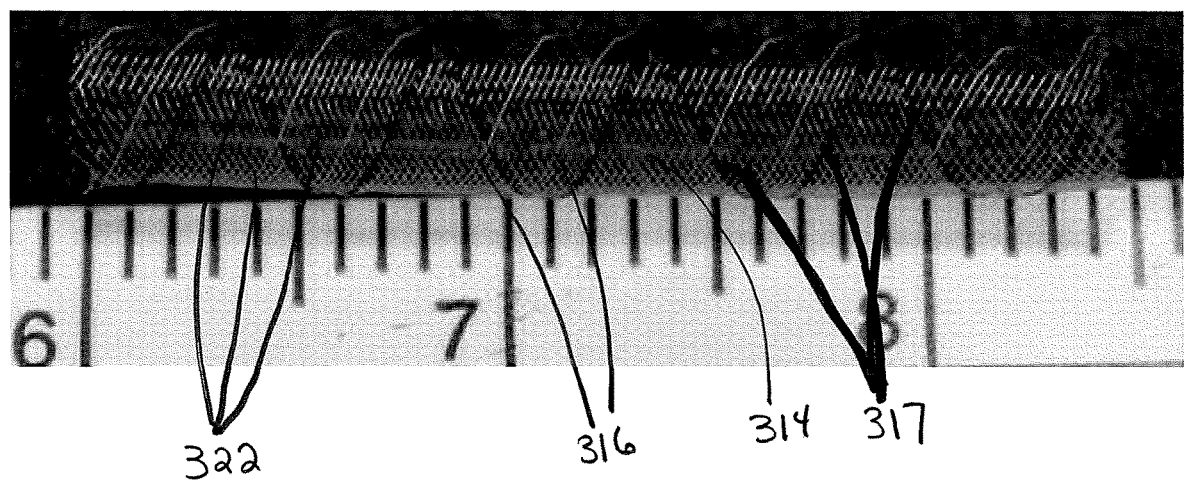
FIG. 8A is a picture of an embodiment of an implantable endovascular device comprising 46 interwoven poly L-lactic acid (PLLA) polymeric fibers and 2 radio-opaque wires.
Figure 8B:
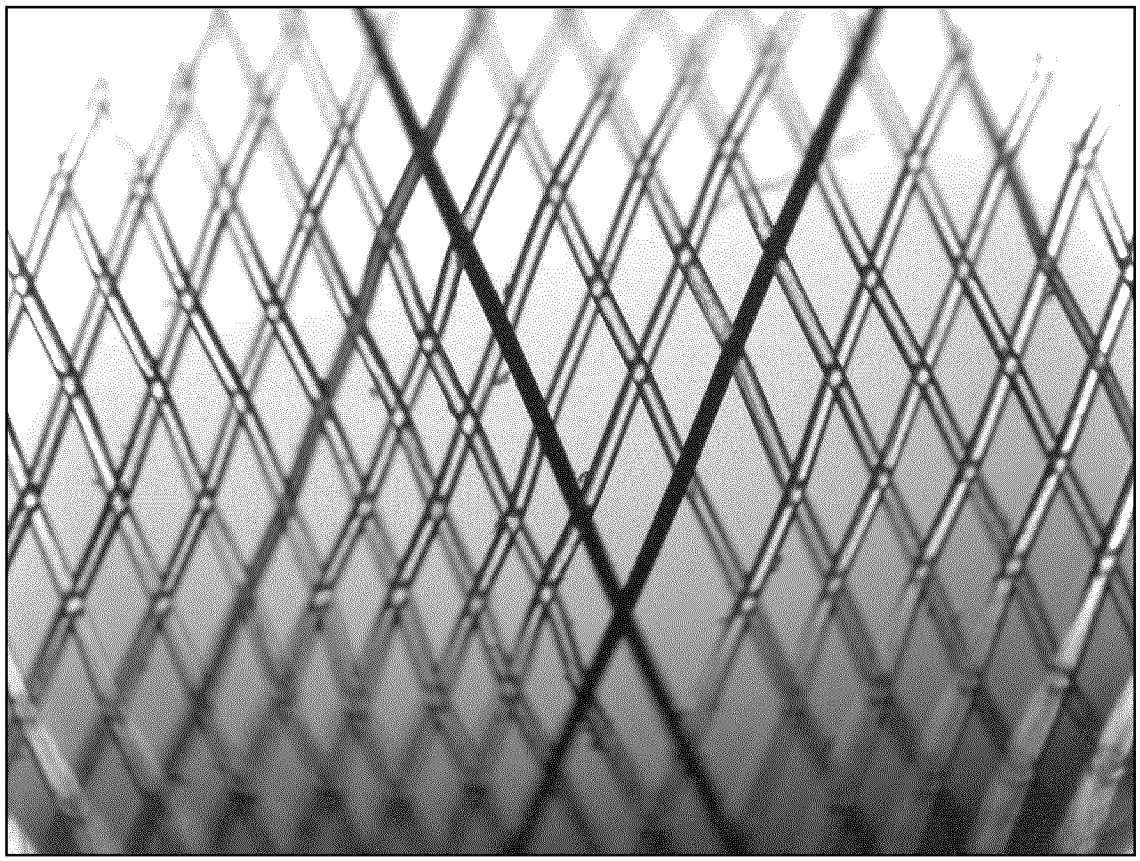
FIG. 8B is a close up picture of the device of FIG. 8A.

Referring to FIG. 8A a device was made constructed with 46 bioabsorbable polymeric fibers of poly-L-lactic acid with a molecular weight of 30;000 g/mol and a diameter of 50 μm interwoven with two radio-opaque fibers of tantalum-coated nitinol. The device was tested in animal blood vessels and was able to keep important vascular side branches open without occluding any of the blood vessels.

While specific embodiments of the invention have been described and illustrated, such embodiments should be considered illustrative of the invention only and not as limiting the invention as construed in accordance with the accompanying claims.

What is claimed is:

1. An endovascular device for positioning in a lumen of an intracranial blood vessel to divert blood flow from an aneurysm of the intracranial blood vessel, the endovascular device comprising:
   a resiliently deformable tubular body comprising a braid having (1) at least 38 interwoven bioabsorbable polymeric fibers and (2) from 2 to 12 resiliently deformable interwoven metal wires,
   wherein the braid has a porosity in a range from 60% to 80% when in an expanded configuration selected to permit a small amount of blood to enter the aneurysm with low velocity which causes thrombosis and occlusion of the aneurysm and permits the aneurysm to heal, and
   wherein the resiliently deformable metal wires are both (1) configured to facilitate and/or maintain radial and/or axial expansion of the polymeric fibers in the tubular body in the lumen and (2) comprise a radio-opaque material configured to facilitate imaging.

2. The device of claim 1, wherein the bioabsorbable polymeric fibers have a diameter in the range of about 30 m to about 80 m.

3. The device of claim 1, wherein the resiliently deformable metal wires comprise a nickel-titanium alloy or a cobalt-chromium-nickel alloy.

4. The device of claim 1, wherein the radio-opaque material comprises a radio-opaque metal.

5. The device of claim 4, wherein the radio-opaque metal is tantalum, gold, platinum, or a combination thereof.

6. The device of claim 1, wherein the polymeric fibers comprise polylactides (PLA), polylactide-co-glycolides (PLGA), poly-DL-lactide (DLPLA), poly(L-Lactic acid), poly-L-lactide (LPLA), poly-L-lactide-co-glycolide (PGA-LPLA), poly-DL-lactide-co-glycolide (PGA-DLPLA), or poly-L-lactide-co-DL-lactide (LPLA-DLPLA).

7. A method of treating an aneurysm of an intracranial blood vessel, the method comprising deploying the endovascular device as defined in claim 1 in the lumen of the intracranial blood vessel at a position proximal to the aneurysm.

8. The endovascular device of claim 1, wherein the braid comprises 38 to 96 bioabsorbable polymeric fibers.

9. The endovascular device of claim 1, wherein the braid comprises at least 44 bioabsorbable polymeric fibers, at least 46 bioabsorbable polymeric fibers, at least 48 bioabsorbable polymeric fibers, at least 72 bioabsorbable polymeric fibers, or at least 96 bioabsorbable polymeric fibers.

10. The endovascular device of claim 1, wherein the braid comprises 44 bioabsorbable polymeric fibers, 46 bioabsorbable polymeric fibers, 48 bioabsorbable polymeric fibers, 72 bioabsorbable polymeric fibers, or 96 bioabsorbable polymeric fibers.

11. The endovascular device of claim 1, wherein the bioabsorbable polymeric fibers have a diameter of at least 30 µm.

12. The endovascular device of claim 1, wherein the bioabsorbable polymeric fibers have a diameter of 40 µm, 50 µm, 60 µm, 70 µm, or 80 µm.

13. The endovascular device of claim 1, wherein a diameter of the tubular body is: 7 mm, wherein bioabsorbable polymeric fibers are interwoven at a pitch angle of 9° or less; 5 mm, wherein bioabsorbable polymeric fibers are interwoven at a pitch angle of 12° or less; 4 mm, wherein bioabsorbable polymeric fibers are interwoven at a pitch angle of 16° or less; or 3 mm, wherein bioabsorbable polymeric fibers are interwoven at a pitch angle of 18° or less.

14. The endovascular device of claim 1, wherein, when the device is in an expanded formation the braid has a pore density in a range of 10 pores/mm$^2$ to 32 pores/mm$^2$.

15. The endovascular device of claim 1, wherein the radio-opaque material comprises iodine or barium.

16. The endovascular device of claim 1, wherein the resiliently deformable metal wires comprise one or more of:
    a nickel-titanium alloy coated with the radio-opaque material;
    a drawn filled tube (DFT) comprising a nickel-titanium alloy exterior and a core comprising the radio-opaque material;
    a DFT comprising an exterior comprising the radio-opaque material and a core comprising a nickel-titanium alloy;
    a cobalt-chromium-nickel alloy coated with the radio-opaque material;
    a DFT comprising a cobalt-chromium-nickel alloy exterior and a core comprising the radio-opaque material; or
    a DFT comprising an exterior comprising the radio-opaque material and a core comprising cobalt-chromium-nickel alloy.

17. The endovascular device of claim 1, wherein the braid is shape set by heating the interwoven bioabsorbable polymeric fibers and the resiliently deformable metal wires of the braid at a temperature which relieves residual stress in the polymeric fibers but not in the metal wires.

18. The endovascular device of claim 1, wherein the polymeric fibers have been shape set but the metal wires have not been shape set.

* * * * *